(12) United States Patent
Kinbarovsky

(10) Patent No.: US 10,380,323 B2
(45) Date of Patent: Aug. 13, 2019

(54) SYSTEM AND METHOD FOR PROVIDING AUDIOVISUAL FEEDBACK

(71) Applicant: Jesse Israel Kinbarovsky, Austin, TX (US)

(72) Inventor: Jesse Israel Kinbarovsky, Austin, TX (US)

(*) Notice: Subject to any disclaimer, the term of this patent is extended or adjusted under 35 U.S.C. 154(b) by 1066 days.

(21) Appl. No.: 14/672,024

(22) Filed: Mar. 27, 2015

(65) Prior Publication Data
US 2016/0283684 A1 Sep. 29, 2016

(51) Int. Cl.
G16H 10/40 (2018.01)
G06F 19/00 (2018.01)

(52) U.S. Cl.
CPC ...... *G06F 19/3418* (2013.01); *G06F 19/3468* (2013.01); *G16H 10/40* (2018.01)

(58) Field of Classification Search
CPC .. G06F 19/3418; G06F 19/3468; G16H 10/40
See application file for complete search history.

(56) References Cited

U.S. PATENT DOCUMENTS

| | | |
|---|---|---|
| 7,399,277 B2 | 7/2008 | Saidara et al. |
| 7,440,786 B2 | 10/2008 | Hockersmith et al. |
| 7,539,533 B2 | 5/2009 | Tran |
| 8,318,096 B2 | 11/2012 | Okuda et al. |
| 8,487,758 B2 | 7/2013 | Istoc |
| 8,501,093 B2 | 8/2013 | Rutkowski et al. |
| 2002/0007249 A1* | 1/2002 | Cranley ............ A61B 5/00 702/24 |
| 2004/0133081 A1 | 7/2004 | Teller et al. |
| 2005/0203360 A1* | 9/2005 | Brauker ............ A61B 5/1468 600/345 |
| 2008/0082339 A1* | 4/2008 | Li .................. A61B 5/14551 704/275 |
| 2009/0082829 A1* | 3/2009 | Panken ............ A61B 5/7475 607/45 |
| 2011/0053121 A1 | 3/2011 | Heaton |
| 2012/0130196 A1 | 5/2012 | Jain et al. |
| 2013/0300645 A1* | 11/2013 | Fedorov ............ G06F 3/01 345/156 |

* cited by examiner

*Primary Examiner* — Jonathan Durant
*Assistant Examiner* — Chad A Newton
(74) *Attorney, Agent, or Firm* — Rafael V Baca; Baca Law Firm, PLLC

(57) ABSTRACT

A health monitoring system for receiving a medical test sample from a donating participant having a chronic disease of a plurality of such participants and includes an audiovisual feedback application engine having a display application. The display application receives the test input signal and generates a feedback audiovisual output signal based on the test input signal. Accordingly, in operation, each feedback audiovisual output signal is displayed on the output device, such as among others the corresponding audio and visual output displays of the output device used by the donating participant and, optionally, the plurality of participants. The feedback application engine generates a continuous audio display and a continuous visual display by combining each consecutive feedback audiovisual signal received to form an electronic audiovisual playback file corresponding to the donating participant for attachment to an electronic medical record.

13 Claims, 27 Drawing Sheets

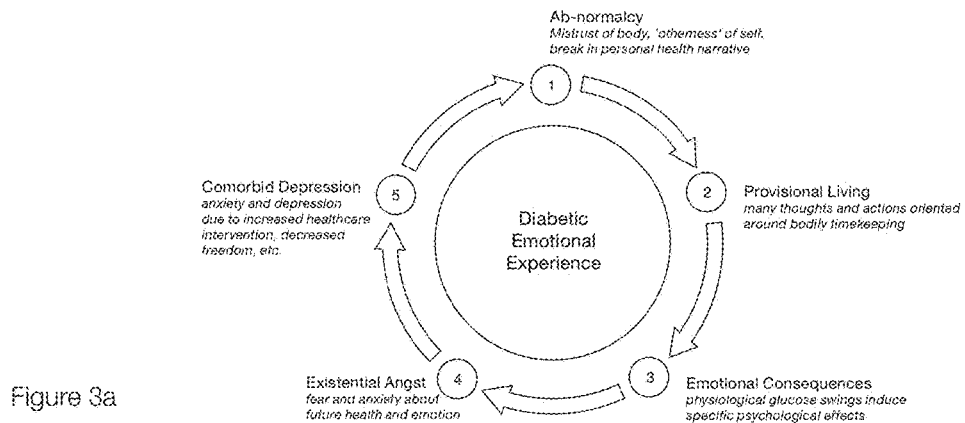
Figure 3a
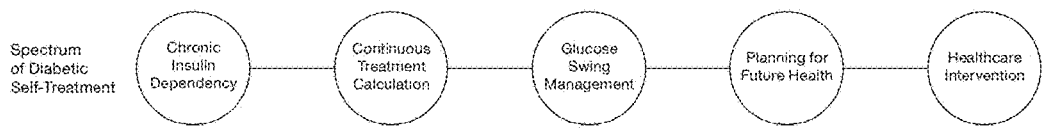
Figure 3b
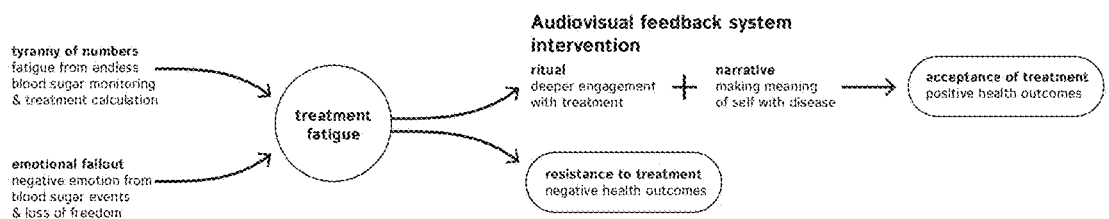
Figure 3c
Figure 3

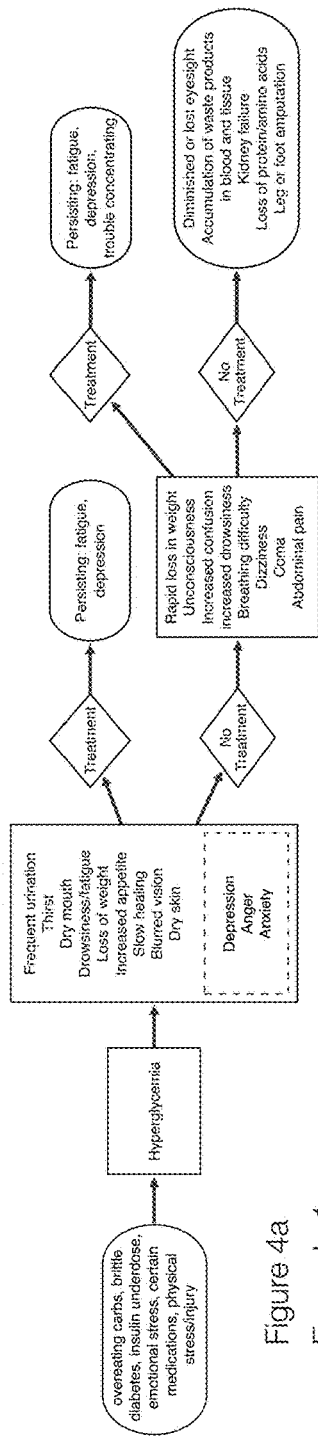
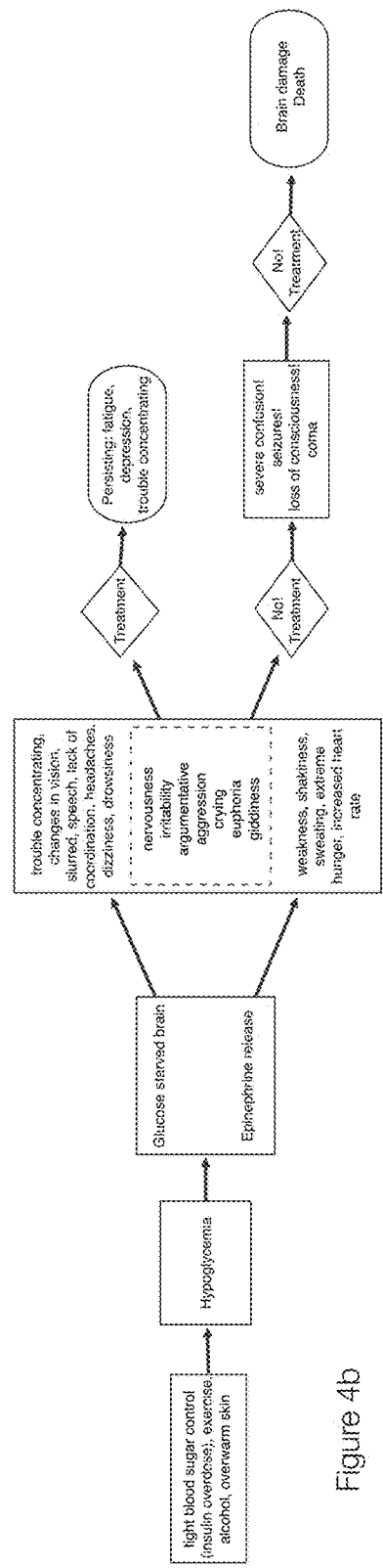
Figure 4

Illustration Audio Visual System
Aplied to mobile interactive device

Illustrative Sequence for Feedback Application

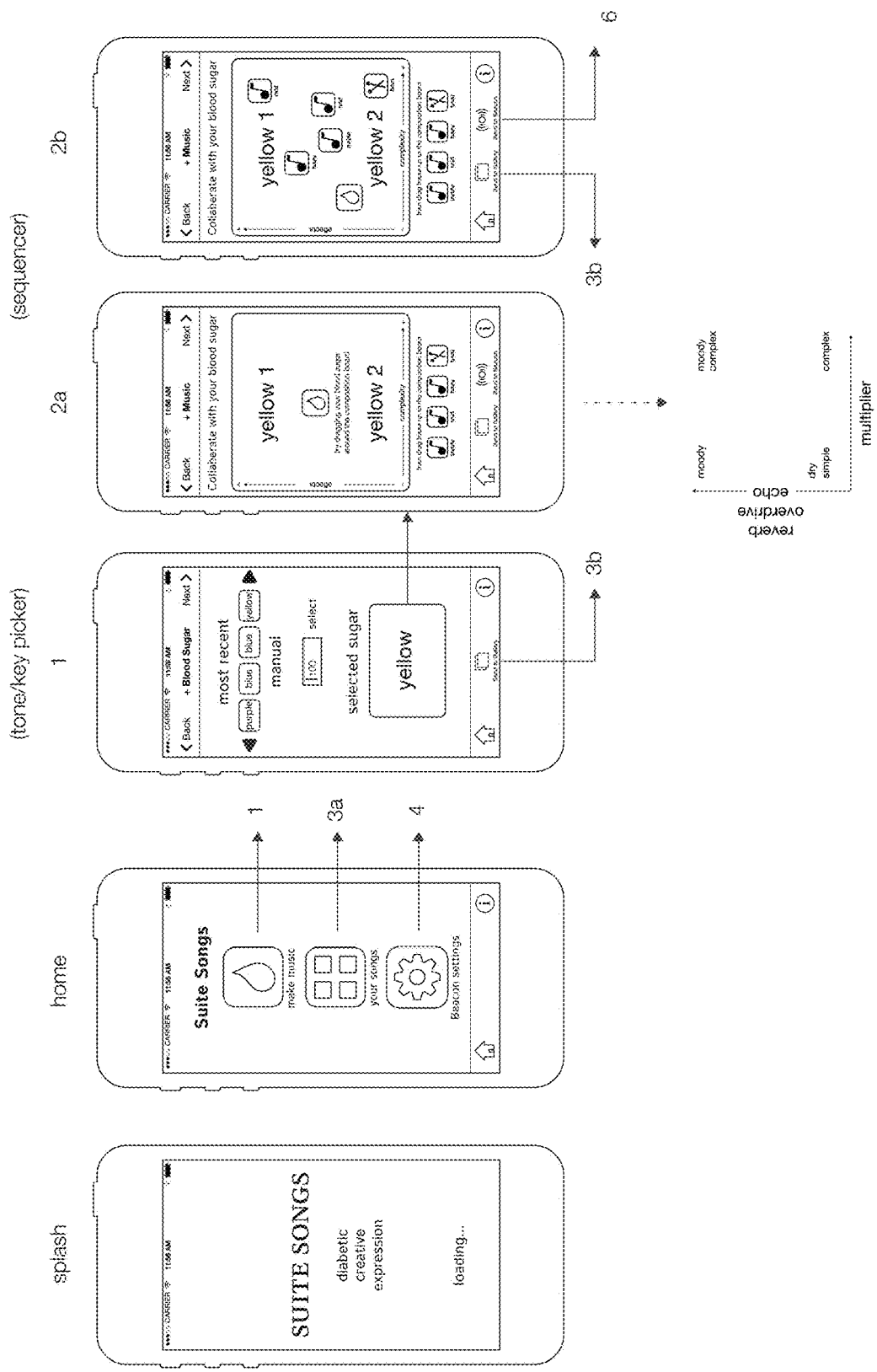
Figure 10 (Figure 10a)

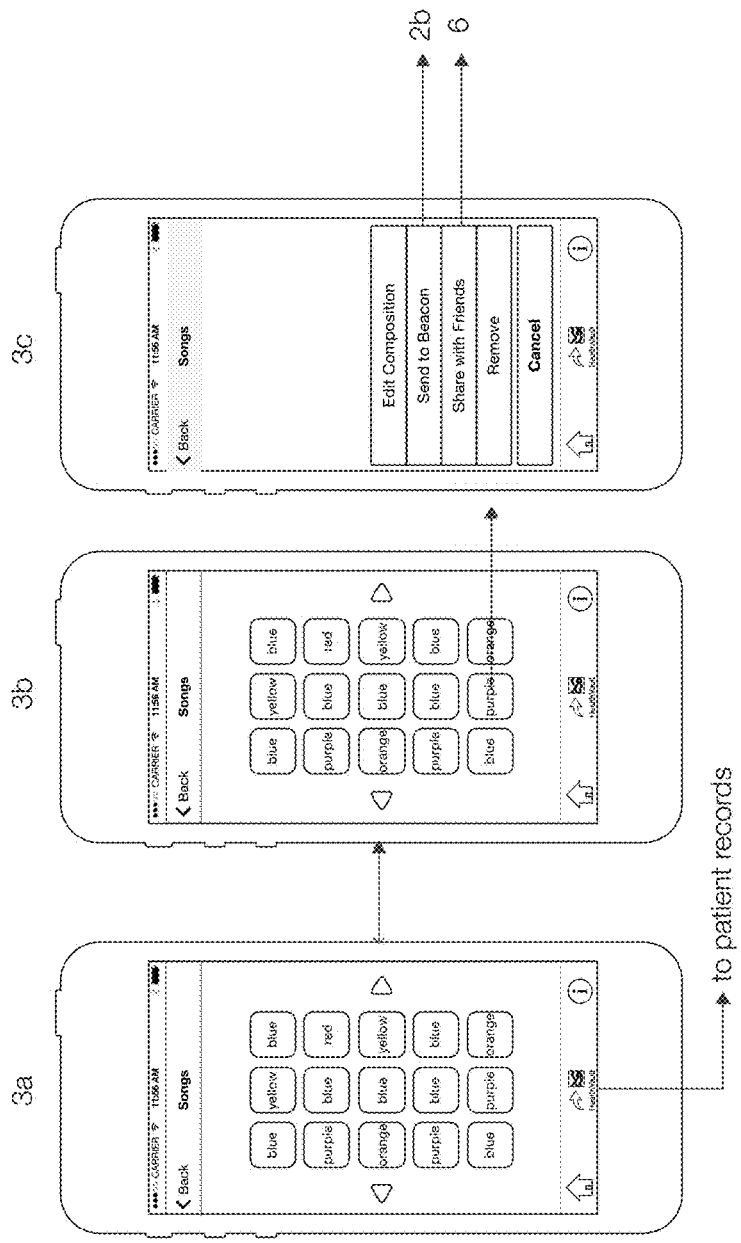
Figure 10 (Figure 10b)

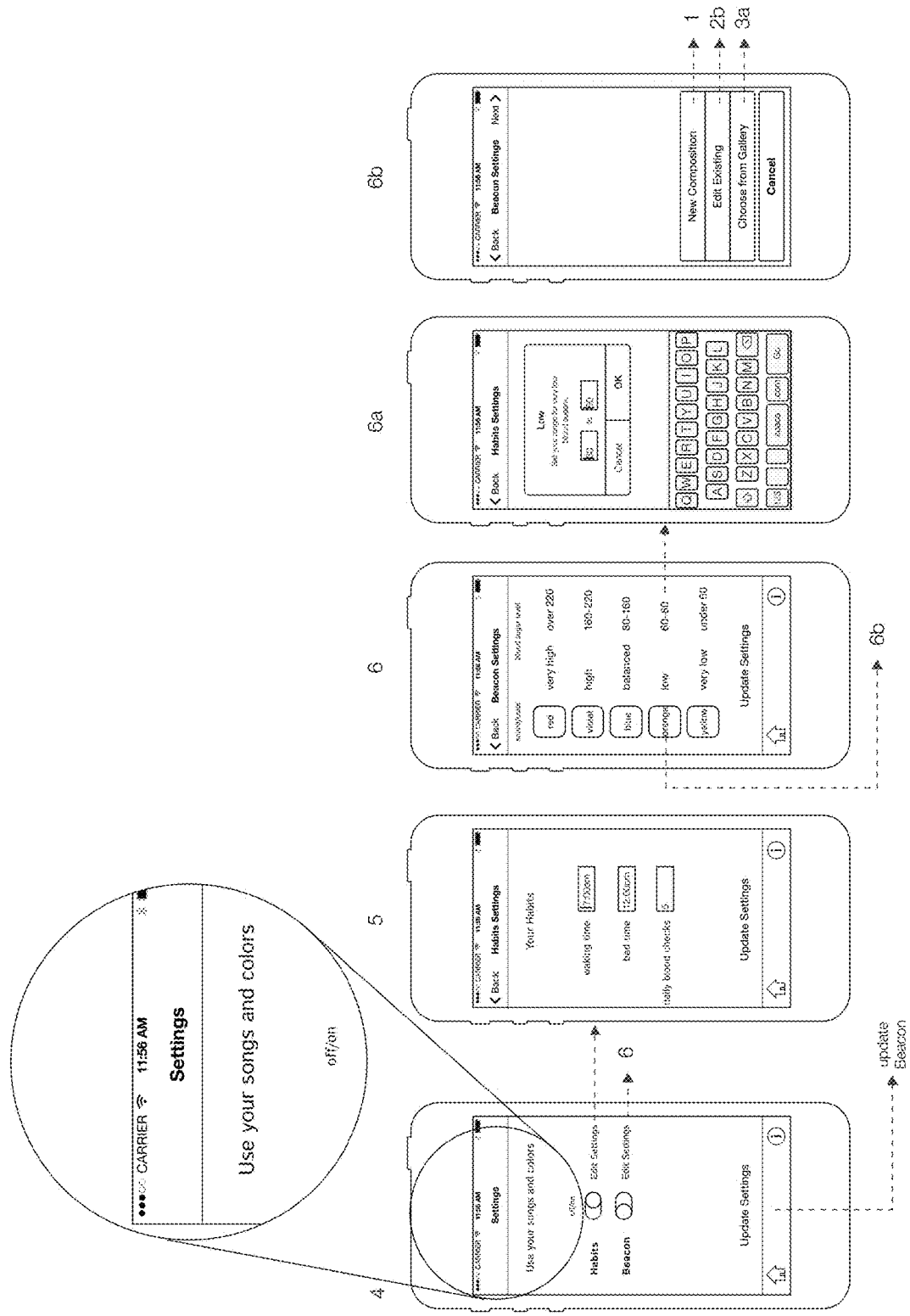
Figure 10 (Figure 10c)

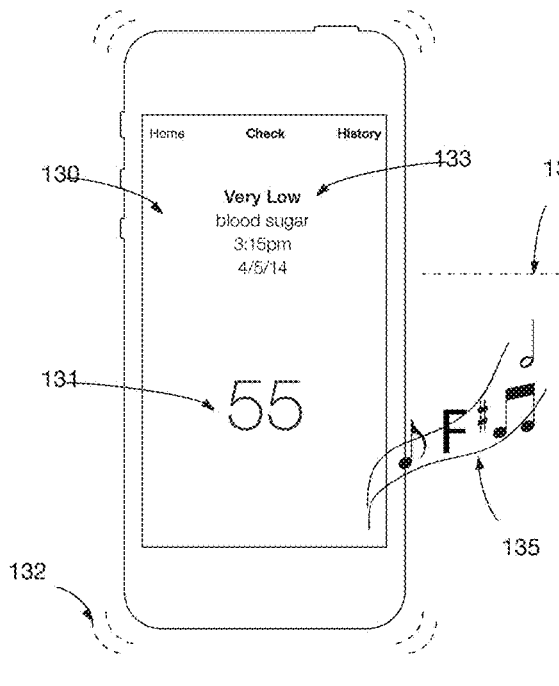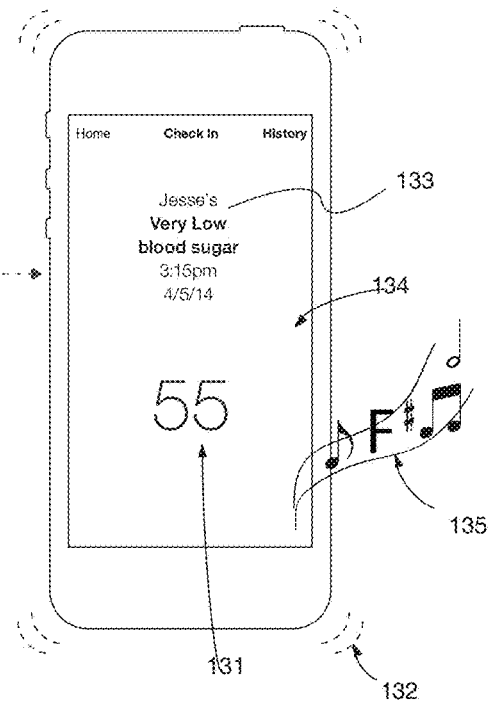
Figure 14a
Figure 14b
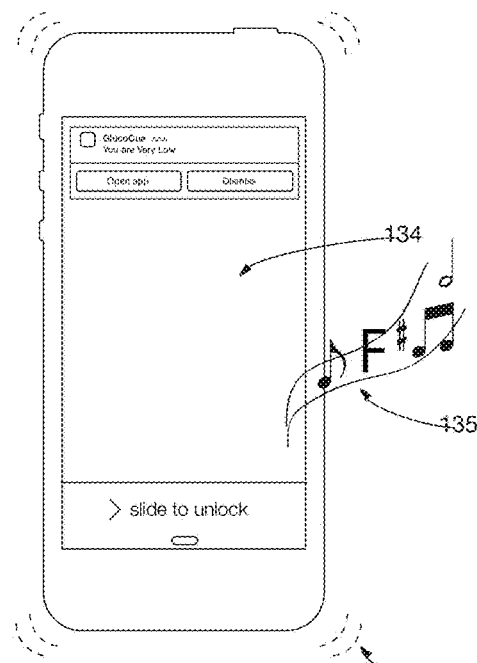
Figure 14
Figure 14c

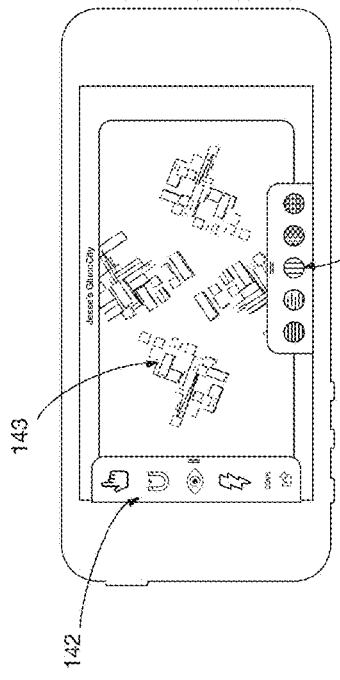
Figure 15b
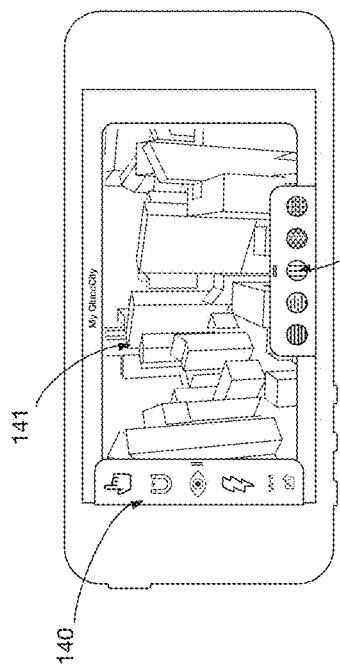
Figure 15a
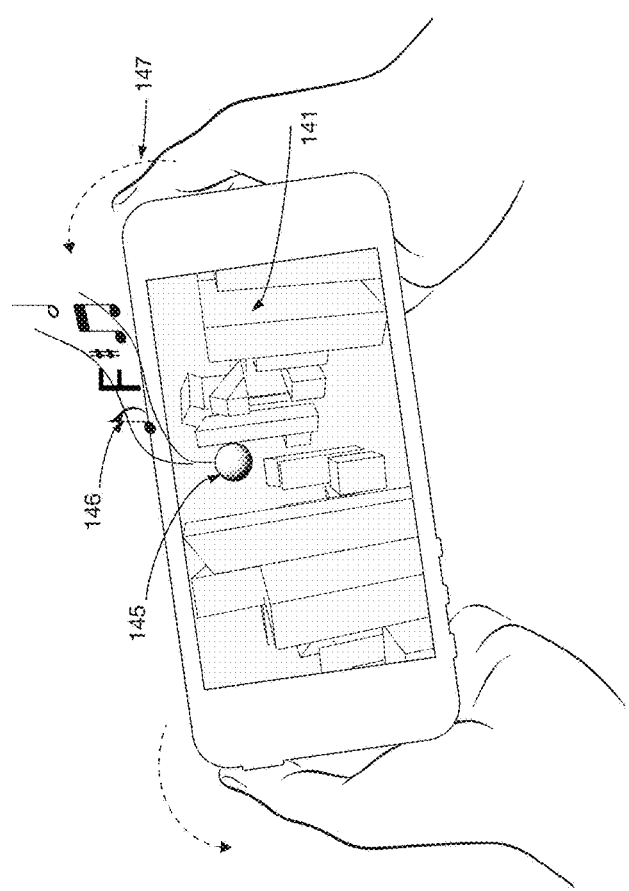
Figure 15c
Figure 15

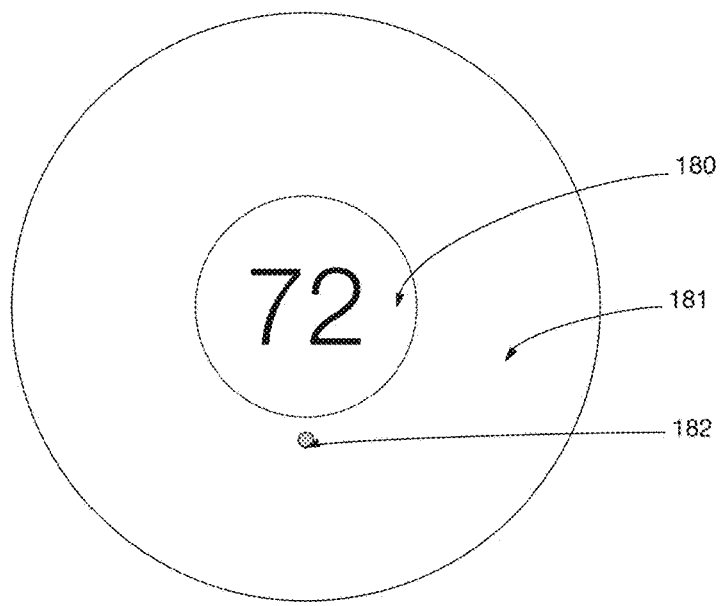
Figure 17a
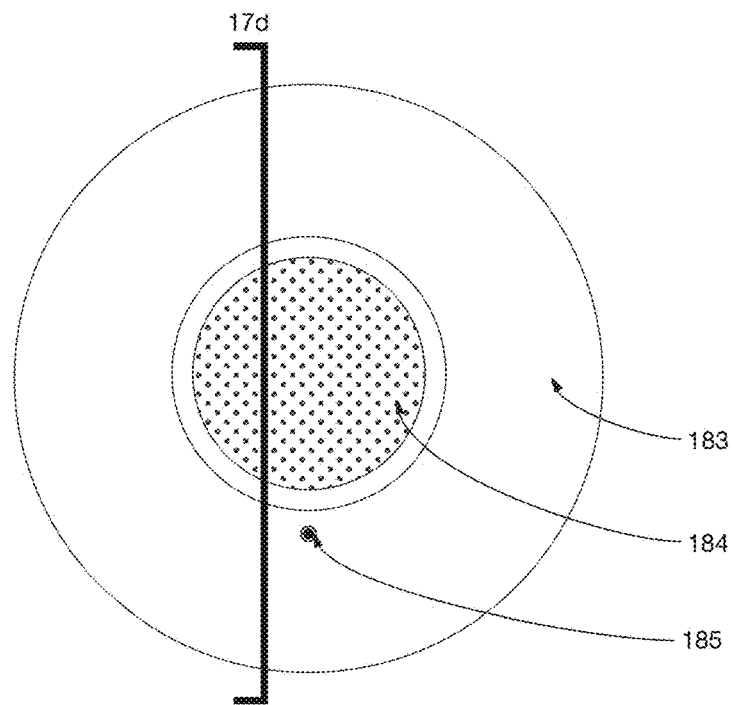
Figure 17b
Figure 17

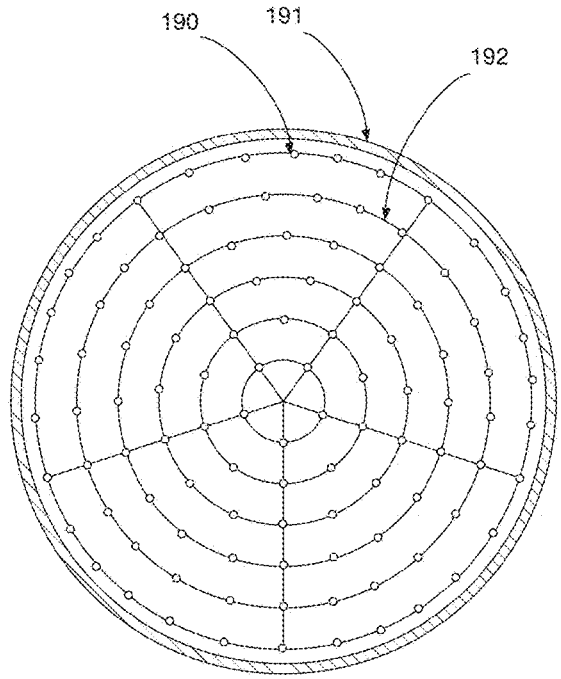
Figure 17c
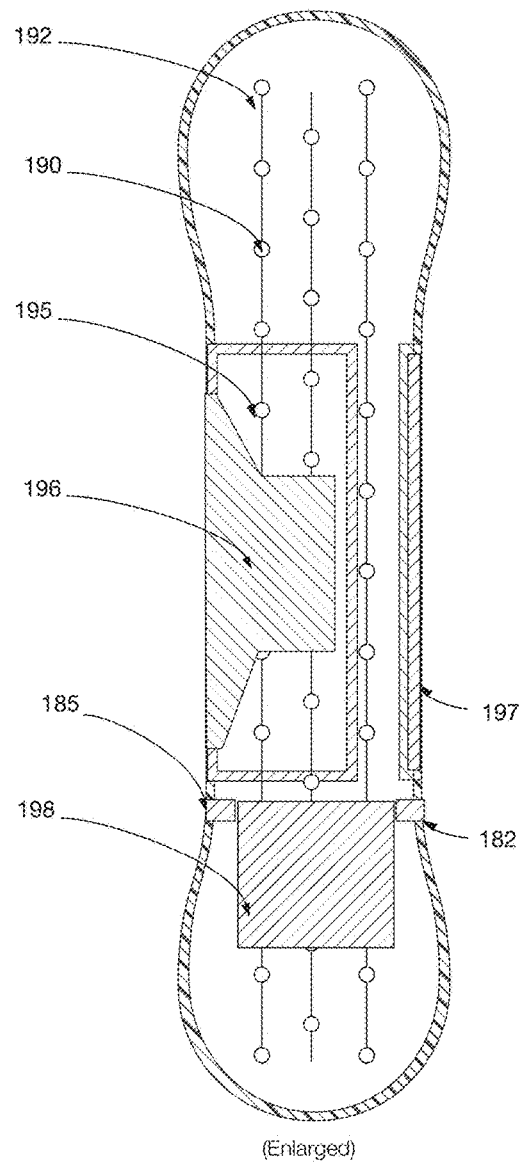
(Enlarged)
Figure 17d
Figure 17

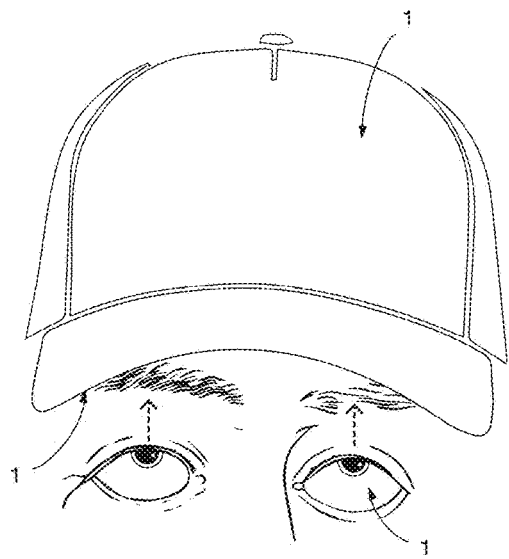
Figure 19a
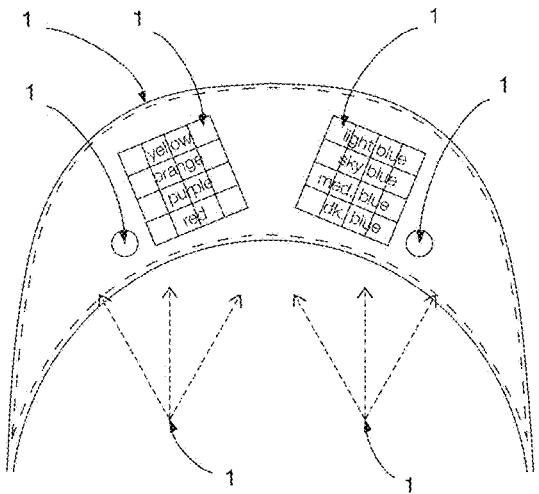
Figure 19b
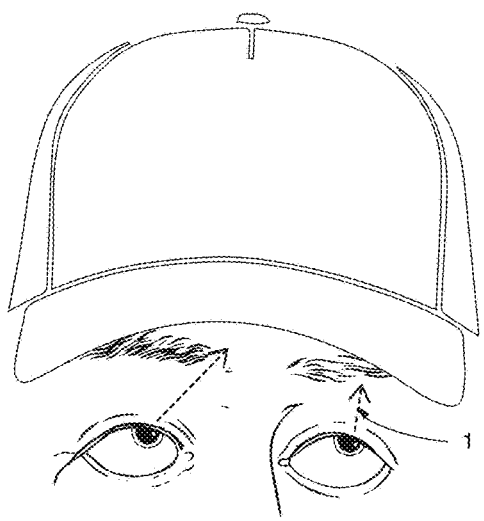
Figure 19c
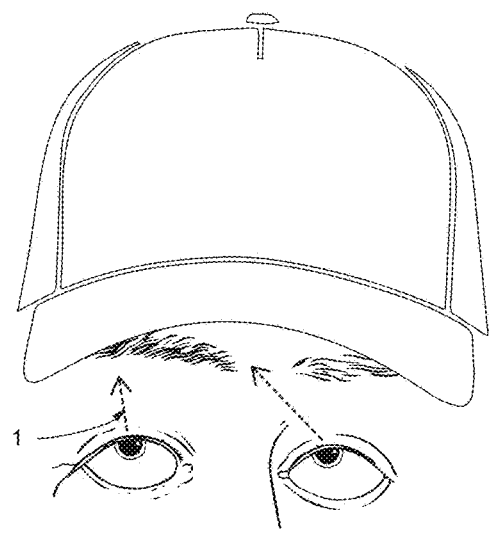
Figure 19d
Figure 19

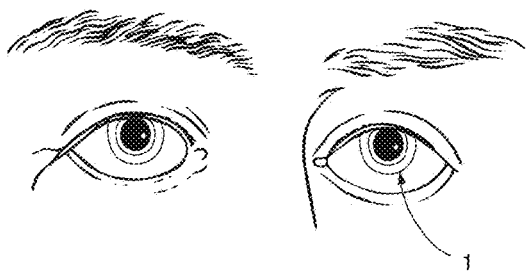
Figure 20a
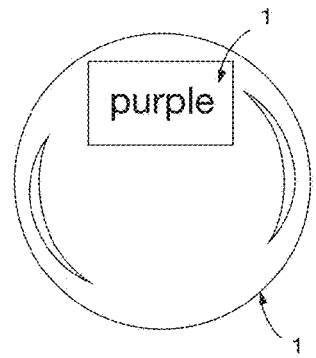
Figure 20b
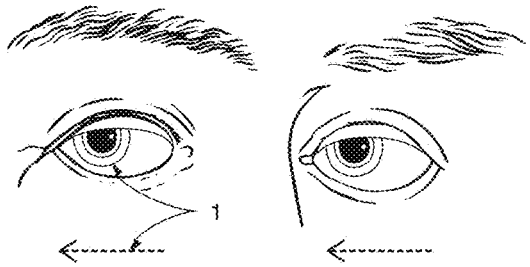
Figure 20c
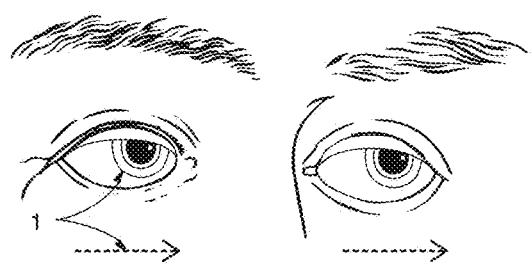
Figure 20d
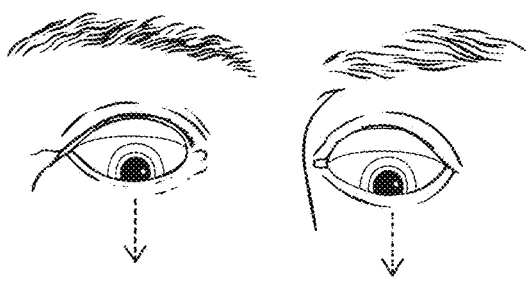
Figure 20e
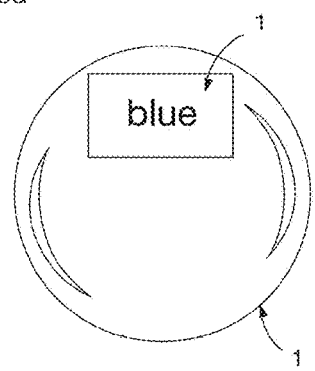
Figure 20f
Figure 20

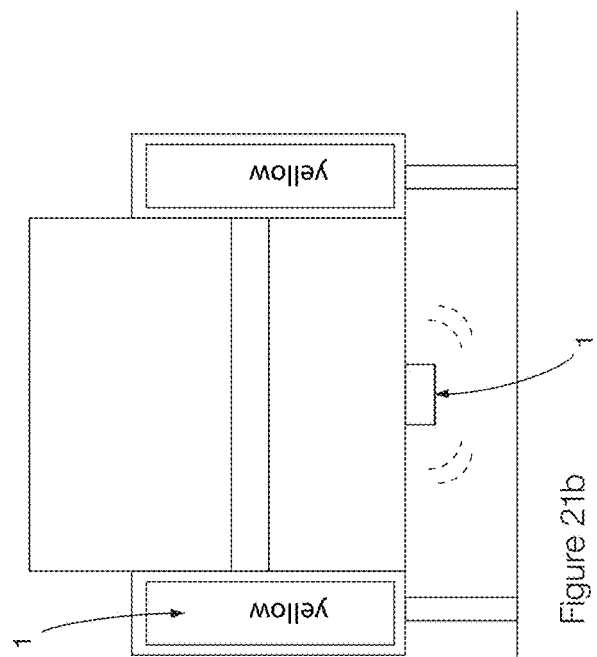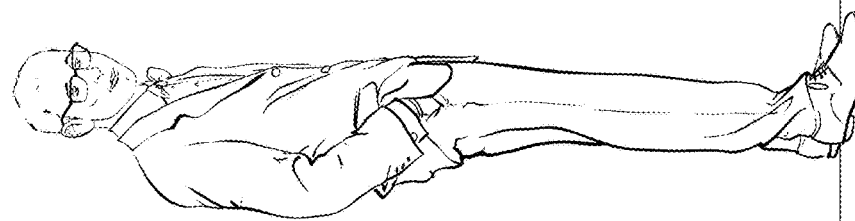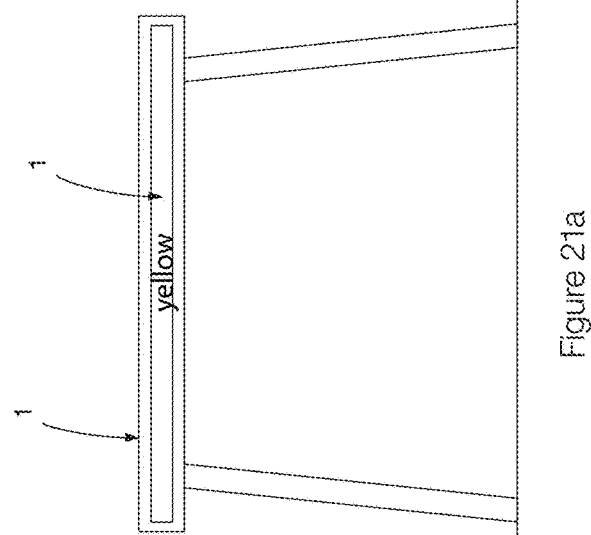
Figure 21

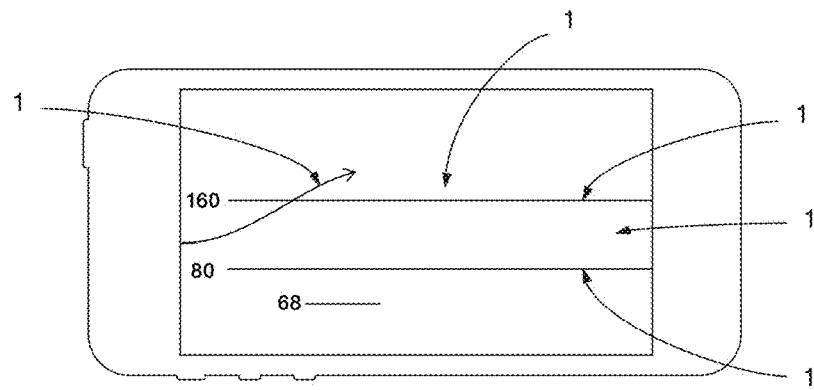
Figure 23a
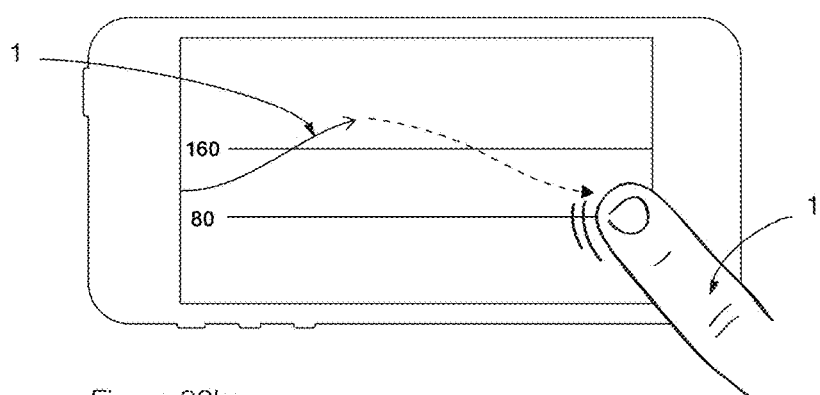
Figure 23b
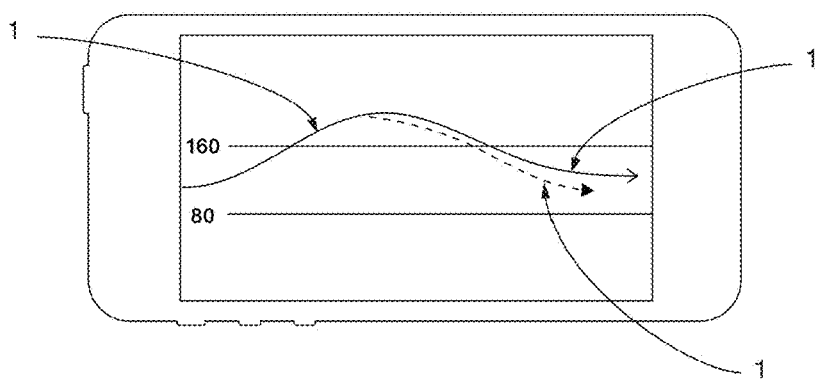
Figure 23c
Figure 23

SYSTEM AND METHOD FOR PROVIDING AUDIOVISUAL FEEDBACK

CROSS REFERENCE TO RELATED APPLICATIONS

This non-provisional utility application claims benefit under 35 U.S.C. § 119(e) from prior U.S. Provisional Patent Application Ser. No. 61/972,173 filed on Mar. 28, 2014 entitled "System and Method for Providing Audiovisual Feedback", by inventor Jesse Kinbarovsky, the entire disclosure of which is hereby incorporated by reference as if fully set forth herein.

TECHNICAL FIELD

The present disclosure relates generally to sensory communication systems for adaptive healthcare provided while monitoring a person's health, and in particular to a system and method for monitoring blood glucose of a participant by providing interactive audiovisual feedback and changes in medicinal dosages based on audiovisual feedback received from the participant, plurality of participant and through interactive gaming methods, whereby permission is granted by the participant to the plurality of participants and through gaming venues in compliance with government regulations regarding electronic protected health information (hereinafter "ePHI") for patients (such regulations as, among others, the *Health Insurance Portability and Accountability Act* (hereafter "HIPAA") (Health Insurance Portability and Accountability Act of 1996 (HIPAA); Public L. 104-191, 101 Stat. 1936, enacted Aug. 21, 1996; The *Health Information Technology for Economic and Clinical Health Act* (HITECH Act) of the American Recovery and Reinvestment Act of 2009 (ARRA), Public L. 111-5, enacted Feb. 17, 2009, and the *Security Standards for the Protection of Electronic Protected Health Information* (the ePHI Security Rule) published Feb. 20, 2003 (45 C.F.R. Part 160 and Part 164, Subparts A and C)).

BACKGROUND

Like most chronic diseases, blood sugar level treatment with insulin for diabetes is fundamentally reliant on patient-management that invariably requires succumbing to a lifestyle of fastidiousness that mandates frequent medical intervention and perpetual personal awareness of changes blood sugar levels and associated physiological conscious state of mind or commonly "moods" or "emotions" to maintain healthy treatment goals. Generally, medical research tends to indicate that a lack of adherence to a regimented daily treatment often manifests in each individual both physically and emotionally and will often curtail one's lifespan while living with such a chronic disease. Specifically, there exists a growing interest within the medical community in considering the relationship between changes in mental status due to chronic diseases, such as among others, hypoglycemia and adherence to treatment and means by which to encourage the positive emotional effects within patients experiencing a chronic illness, such as among others diabetes, to thereby encourage positive personal long-term treatment practices of the disease by the chronically ill patient.

Presently, despite the relationship between good physiological as well as emotional health, the healthcare product marketplace provides few options for managing the emotional aspects of a chronic physiological illness, and even fewer options are available to diabetics. As the healthcare industry moves toward a more proactive-patient approach, and wireless personal health monitor consumer technologies gain considerable traction in the current market, the healthcare environment is ripe for innovation in its approach to patient-led treatment for chronic illnesses. Unfortunately, there is no known means for an individual diagnosed with a chronic disease to intuitively interact with treating their disease in a long term, non-numerical means that includes gaming and encouraging feedback from an internet-based community of participants.

For example, there exists a need for an intuitive self-therapy that is interactive and improves on the self-narrative of treatment including those patients that are numerically adverse, lack temporal rigor, and lack emotional diligence for a disease with a perpetual plan for treatment. A need exists for an intuitive means for providing numerical medical readings that further promotes meaningful participation and interest by the patient over long periods of the disease narrative. Accordingly, there is a need for a multi-disciplinary approach to this intuitive solution (including, among others, internal medicine, neuroscience, sociology, computer science and design) through interacting with music and color, among other means, with a mobile device based system for monitoring a patients physiological and emotional state to improve their means for managing their chronic disease. Accordingly, there is a need for a system and method that integrates with a blood glucose monitor that is well known in the industry and receives audiovisual feedback from a diabetic participant to actively change their treatment in real time.

BRIEF DESCRIPTION OF THE FIGURES

The accompanying figures, where like reference numerals refer to identical or functionally similar elements throughout the separate views, together with the detailed description below, are incorporated in and form part of the specification and serve to further illustrate various embodiments of concepts that include the claimed invention, and to explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help improve understanding of various embodiments. In addition, the description and drawings do not necessarily require the order illustrated. It will be further appreciated that certain actions and/or steps may be described or depicted in a particular order of occurrence while those skilled in the art will understand that such specificity with respect to sequence is not actually required.

Generally FIG. 3, is a schematic diagram illustrating one exemplary embodiment of a mood display of a chronic disease sufferer as related to the chemical levels of analyte that physiologically corresponds to the sufferers mood or emotional display as a function of time, specifically FIG. 3a shows one illustrative diagram of a diabetic's emotional experience and resulting fatigue and emotional depression, and FIG. 3b shows one illustrative diagram of an health monitoring system responsive to fatigue and depression experienced by the chronic disease sufferer;

Generally, FIG. 4 is a schematic diagram illustrating one exemplary embodiment of a mood display of a chronic disease sufferer as related to the chemical state of hypoglycemia that physiologically corresponds to the sufferers experience display as a function of time, specifically FIG. 4a shows one illustrative diagram of a diabetic's emotional experience and resulting fatigue, emotional depression, and with difficulty breathing, and FIG. 4b shows one illustrative diagram of a diabetic's emotional experience and resulting lack of concentration, irritability, and physiological display such as shakiness and sweating;

Generally, FIG. 5a illustrates one exemplary embodiment of predetermined color assignment to blood glucose correlation with physiological emotion for use by the audiovisual feedback system; FIG. 5b illustrates one exemplary embodiment of predetermined musical keys assignment to blood glucose correlation with physiological emotion for use by the audiovisual feedback system, and FIG. 5c illustrates one exemplary embodiment of predetermined color assignment and predetermined musical keys assignment to blood glucose correlation with physiological emotion for use by the audiovisual feedback system;

Generally, FIG. 6 shows both a predetermined color assignment and a predetermined musical keys assignment to blood glucose correlation with physiological mood for use by the audiovisual feedback system;

Generally, FIG. 7a shows a board display that illustratively plots mental state or, commonly, "emotional" levels attributed from ongoing hypoglycemia, FIG. 7b shows predetermined colors that are mapped to the board display of FIG. 7a attributable to the mental states of the chronically ill donating participant, and FIG. 7c illustrates predetermined musical notes that are mapped to the board display of FIG. 7a;

Generally, FIG. 10 is a schematic flow diagram showing one exemplary embodiment of operations of an audiovisual feedback system as applied to a mobile interactive display device that illustrates one illustrative method for feedback application by at least one participant, specifically, FIG. 10a illustrates an operational flow of the audiovisual feedback system, via a mobile interactive display device, for a donating participant to make musical compositions and visual display compositions based on a series of test outputs provided by the donating participant to the audiovisual feedback system, FIG. 10b illustrates an operational flow of the audiovisual feedback system for inserting the donating participant's musical compositions and visual display compositions as ePHI into a corresponding physicians electronic medical record that serves as the donating participant's electronic medical chart; and FIG. 10c illustrates operational flow of the audiovisual feedback system for receiving, at least in part, a feedback audiovisual input signal from the the eye movement of the donating participant (as also shown in FIG. 11 below);

Generally, FIG. 11a shows the audiovisual feedback system providing feedback audiovisual output signals including a donating participant's musical compositions and visual display compositions to a mobile interactive display device, FIG. 11b shows an audiovisual feedback system receiving, at a mobile interactive display device, a feedback audiovisual input signal illustrated as a responsive audio F Minor input from the donating participant and a feedback audiovisual input signal illustrated as a responsive visual input as, for example, three-dimensional sensory monitoring of an eye ball's cornea within a spatial reference frame as well as sensory monitoring of an eye with infrared tracking of the lens of an eyeball relative to its retina (to select a responsive predetermined color, see further below for more detail) relative to the output device, shown as a mobile interactive display device, FIG. 11b' shows a second feedback audiovisual output signal responsive to a trigger arising from receipt of the feedback audiovisual input signal, the second feedback audiovisual output signal illustrated as a F major musical key in the continuing musical composition of the donating participant to thereby increase the level of insulin of the donating participant in response to the feedback audiovisual signal received by the donating participant, FIG. 11c shows an audiovisual feedback system receiving, at a plurality of mobile interactive display devices, a plurality of feedback audiovisual input signals, illustrated as a responsive audio F Minor input from the donating participant and a feedback audiovisual input signal illustrated as a responsive visual input as retinal movement (to select a responsive predetermined color) relative to the output device and as a responsive B major input from another participant from the plurality of participants authorized by the donating participant in compliance with government regulations regarding ePHI to participate in the donating participant's treatment, FIG. 11c' shows a second feedback audiovisual output signal in responsive to a trigger arising from receipt of the feedback audiovisual input signals from both the donating participant and another authorized participant as shown, the second feedback audiovisual output signal illustrated as a F major musical key in the continuing musical composition of the donating participant to thereby increase the level of insulin of the donating participant in response to the feedback audiovisual signal received by the donating participant;

Generally.

FIG. 14 is a schematic diagram illustrating one exemplary embodiment of a donating participant interacting with at least one personal area network interactive display device of a health monitoring system;

FIG. 15 is a schematic diagram illustrating one exemplary embodiment of a donating participant interacting with a plurality of output devices of a health monitoring system;

FIG. 16 and FIG. 17 illustrate different embodiments of a social output device of FIG. 15. FIG. 16a is a cross-sectional view of the social output device of FIG. 16. FIG. 17a is a cross-sectional view of the social output device of FIG. 17;

Generally, FIG. 19 is a schematic diagram illustrating one exemplary embodiment of a donating participant interacting with a mobile interactive display device of a health monitoring system, specifically, in FIG. 19a, the donating participant receives a feedback audiovisual output signal to change their medicinal intake, in FIG. 19b, the donating participant provides a plurality of feedback input audiovisual signals to the mobile interactive display device, in FIG. 19c, the donating participant provides a plurality of feedback input audiovisual signals to the mobile interactive display device;

Generally, FIG. 20 is a schematic diagram that shows mobile interactive display device 81 coupled to one embodiment of a medical testing input system 20, shown in FIG. 20a, having a housing 881, a universal test transceiver 67 integrated with the housing 881 and a gateway interface 62 for insertion into a receiving port 81a, shown in FIG. 20b;

FIG. 23 is one exemplary embodiment of a game; and

Generally, FIG. 24 is one exemplary embodiment of a game; FIG. 24a shows a balloon 444 within a bubble field 445, FIG. 24a show a balloon 444 being manipulated to move within the bubble field 24b; and FIG. 24c shows a balloon 444 achieving a safe zone.

Figure 1:
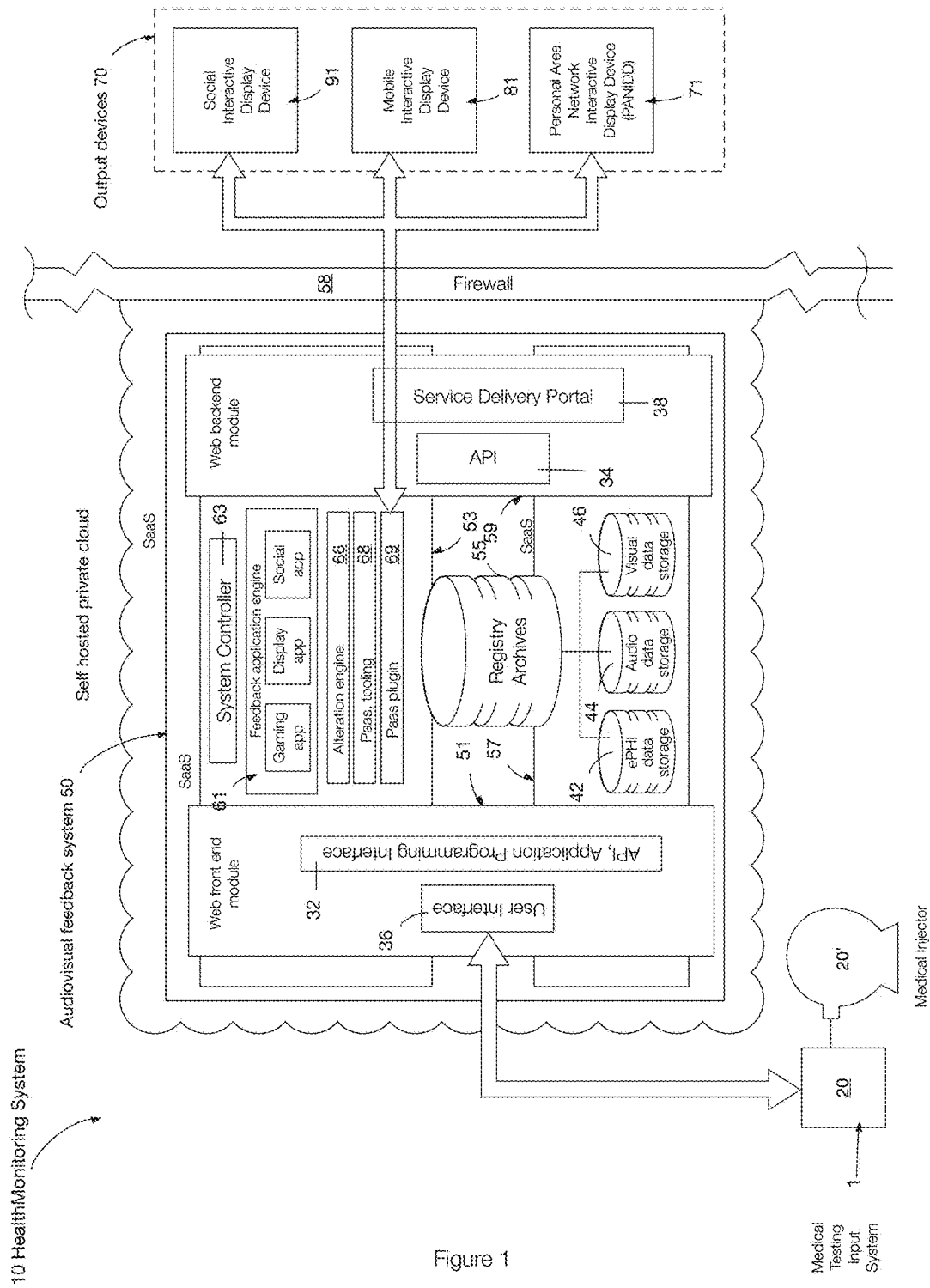
FIG. 1, in general, is a system diagram health monitoring system in accordance with embodiments of the present disclosure featuring a cloud-based audiovisual feedback system for interfacing with a participant donating a medical test sample as part of treating that participant's chronic disease and, optionally, a plurality of participants invited by the donating participant to provide feedback to the audiovisual feedback system with respect to treating the donating patient's chronic disease, the cloud-based audiovisual feedback system features at least one Software as a Service (SaaS) application that electronically provides an audio and visual output display for receiving audio and visual feedback from the donating participant, a plurality of authorized participants through a game or through electronic information input for encouraging positive treatment behavior of the donating participant whereby the audiovisual feedback system provides a change in the rate of medication delivered to the donating participant, an audiovisual playback file corresponding to the participants treatment over time in the form of a musical composition including a rhythm, melody, harmony and, optional lyrics, and a moving image composition featuring predetermined images such as colors, scenes, individuals and animals as well as objects, each derived through interacting with the audiovisual feedback system, to effectuate treatment of the patient in an emotionally stimulating, encouraging manner during the perpetual course of treating the associated chronic disease.

Apparatus and method components have been represented where appropriate by conventional symbols in the drawings, showing only those specific details that are pertinent to understanding the various embodiments so as not to obscure the disclosure with details that will be readily apparent to those of ordinary skill in the art having the benefit of the description herein. Thus, it will be appreciated that for simplicity and clarity of illustration, common and well-understood elements that are useful or necessary in a commercially feasible embodiment may not be depicted in order to facilitate a less obstructed view of these various embodiments.

DETAILED DESCRIPTION

Generally speaking, pursuant to the various embodiments, the present disclosure provides a health monitoring system for receiving a medical test sample from a donating participant having a chronic disease of a plurality of such participants. Those of ordinary skill in the art will readily recognize other application of the health monitoring system to other chronic illnesses such as, among others, cancer, high blood pressure, heart disease, autoimmune diseases such as AIDs and arthritis, asthma, obesity, tobacco and alcohol use. For purposes of illustration in this application, the health monitoring system blood is applied to a glucose monitoring system for example. Accordingly, the blood glucose monitoring system communicatively connects with a standard blood glucose meter for receiving a medical test blood sample from a donating participant from a plurality of participants. The blood glucose monitoring system includes a medical testing input system, a computer based audiovisual feedback system and at least one output device.

In particular, the medical testing input system is coupled to the standard blood glucose meter. Operatively, the blood glucose meter receives the medical test blood sample and provides a test output to the medical testing input system. The audiovisual feedback system receives a test input signal from the medical testing input system. The medical testing input system generates the test input signal based on the medical test blood sample.

The audiovisual feedback system includes a registry archive that is communicatively connected to the plurality of participants, a feedback application engine that is communicatively connected to the registry archive, an alteration engine that is communicatively connected to the feedback application engine, and the registry archive, and a system controller that is communicatively connected to the alteration engine, the feedback application engine, and the registry archive. In one exemplary embodiment the system controller comprises a control processor.

The audiovisual feedback application engine includes a display application. The display application receives the test input signal and generates a feedback audiovisual output signal based on the test input signal. Accordingly, in operation, each feedback audiovisual output signal is displayed on the output device, such as among others the corresponding audio and visual output displays of the output device used by the donating participant and, optionally, the plurality of participants. In one embodiment, the feedback application engine generates a continuous audio display and a continuous visual display by combining each consecutive feedback audiovisual signal received to form an electronic audiovisual playback file corresponding to the donating participant.

With reference to the output devices, each output device is communicatively connected to the computer based audiovisual feedback system. As shown, the output devices can be a mobile interface display device, a social interactive display device, and a personal area network display device (PANIDD). Generally, the at least one output device receives the feedback audiovisual output signal and provides an audio and visual output display based on the test output of the donating participant.

The audio and visual output display is based on a continuity of predetermined musical tones and predetermined colors, respectively. Each tone and color corresponds to a predetermined mental state or, commonly, physical "emotion" or "mood" experienced by the donating participant at the time the medical test blood sample is received by the medical testing input system as a function of blood glucose level.

In operation, the donating participant provides a feedback audiovisual input signal, based on the feedback audiovisual output signal, to the alternation engine, via the output device. The alteration engine, responsive to the feedback audiovisual input signal, generates a command signal to thereby trigger the system controller.

In one embodiment, the system controller provides a controller signal, based on the command signal, to the audio and visual output display of the output device. The system controller operates the output device to warn the donating participant to manually control the rate of medication provided to the donating participant via a responsive, second feedback audiovisual output signal having predetermined audiovisual alerting information.

The system controller provides a controller signal, based on the command signal, to medical input testing system, the medial input testing system coupled to a medicinal injector, the system controller operates the medicinal injector responsive to the controller signal to control the rate of medication provided to the donating participant responsive to the feedback audiovisual input signal. In one embodiment, the medicinal injector comprises an insulin pump.

The audiovisual feedback system further includes a social application. The social application is communicatively coupled to the registry archives, display application, the alteration engine, and the system controller. Operatively, another participant from the plurality of participants provides a feedback audiovisual input signal, based on the feedback audiovisual output signal of the donating participant, to the alternation engine, via the output device. Thus, the alteration engine, responsive to the feedback audiovisual input signal, generates a command signal to trigger the system controller to control the rate of medication provided to the donating participant responsive to the feedback audiovisual input signal of the another participant.

In one aspect, the audiovisual feedback system further includes a gaming application and a social application, each communicatively coupled to the registry archives, display application, the alteration engine, and the system controller. With respect to the gaming application, the donating participant and the plurality of participants access the gaming application, based on a game generated by the gaming application. The gaming application generates a game controlled feedback audiovisual input signal, based on the game, to the alternation engine. The alteration engine generates a command signal to trigger the system controller to control the rate of medication provided to the donating participant responsive to the game controlled feedback audiovisual input signal.

Skilled artisans will appreciate that elements in the figures are illustrated for simplicity and clarity and have not necessarily been drawn to scale. For example, the dimensions of some of the elements in the figures may be exaggerated relative to other elements to help improve understanding of various embodiments. In addition, the description and drawings do not necessarily require the order illustrated. It will be further appreciated that certain actions and/or steps may be described or depicted in a particular order of occurrence while those skilled in the art will understand that such specificity with respect to sequence is not actually required.

Apparatus and method components have been represented where appropriate by conventional symbols in the drawings, showing only those specific details that are pertinent to understanding the various embodiments so as not to obscure the disclosure with details that will be readily apparent to those of ordinary skill in the art having the benefit of the description herein. Thus, it will be appreciated that for simplicity and clarity of illustration, common and well-understood elements that are useful or necessary in a commercially feasible embodiment may not be depicted in order to facilitate a less obstructed view of these various embodiments.

Illustrative embodiments of the present disclosure and appended claims, as described below, are generally applicable to the ePHI-compliant gatekeeper system that includes user equipment (UE), a cloud-based audiovisual feedback system, and a plurality of networks. In one aspect, the plurality of networks includes networks based on network infrastructure of a type well known in the industry, such as internet protocol network architecture, TCP/IP. Each of the plurality of networks based on infrastructure well known in the industry includes, among others, a number of infrastructure devices for facilitating communications for the user equipment and operating in the system. Such infrastructure devices include elements of a radio access network (RAN) or simply access network that communicate with the subscriber units via an air interface, such as for instance, eNodeBs, base radios, base stations, base transceiver stations, and the like. Such infrastructure devices further include elements of an infrastructure core (e.g., a UMTS-3G core network for a 3G or GSM/EDGE system; an Evolved Packet Core (EPC) in an LTE system etc.) used to manage the allocation of radio resources of the network, with the infrastructure core including elements such as for instance, Mobility Management Entities, Signaling Gateways, Health Level 7 (HL7) MTS adapter core engines, Packet Data Network Gateways, etc. Other infrastructure devices that may be included in any one or each of the disclosed networks includes, but are not limited to, switches, zone controllers, base station controllers, repeaters, access points, routers, etc.

In one aspect, the plurality of platformed networks of the ePHI-compliant gatekeeper system includes networks based on network infrastructure of a type well known in the industry, such as internet protocol network architecture, TCP/IP. Illustratively, in one embodiment among others, the plurality of platform networks includes any combination of a pharmacy network, a social network, a hospital/clinical network, an imaging center network, a radiologic network, and a virtual private network such as among others a Picture Archiving and Communication System (PACs).

Illustratively, and at least in one aspect, each network from the plurality of platformed networks may comprise either a private 3G or GSM/EDGE system for supporting HL7 such as among others a hospital network 3G system or a public 3G system such as among others a commercial carrier commercial mobile phone EDGE system. Alternatively, each network from the plurality of platformed networks may comprise either a private 4G Long Term Evolution (LTE) system for supporting m-health, such as among others a hospital network 4G LTE system or a public 4G LTE system, such as among others a commercial carrier for mobile 4G LTE systems.

In at least one aspect, the plurality of platformed networks may include at least one network includes an International Mobile Telecommunications-2000 (IMT2000) based network designed to meet IMT-2000 standards, such as among others a private radiologic imaging center or a public 3G system, such as among other a commercial carrier mobile 3G systems. However, the plurality of networks can comprise any combination of 3GPP ($3^{rd}$ Generation Partnership Project), broadband, legacy or non-3GPP radio access type systems including but not limited to LTE systems, Wireless Local Area Network (WLAN) systems, and Code Division Multiple Access (CDMA) systems, GPRS (general packet radio service) systems, Land Mobile Radio (LMR) systems, and WiMAX (Worldwide Interoperability for Microwave Access) systems. Among other messaging applications, mobile devices and other telecommunication systems are increasingly relying on internet protocols such as Session Initiation Protocol (SIP) for creating, modifying, and terminating communication sessions with one or more participants using a combination of multimedia applications, such as for voice and video.

In one aspect, the cloud-based audiovisual feedback system is based on cloud computing infrastructure. Cloud computing refers to the practice of storing regularly used computer data on multiple servers that can be accessed through the Internet and the practice of providing computer based application functions with multiple servers accessed through the internet computer data as applied to data received by the application functions. For purposes of illustration in this disclosure and appended claims, the cloud-based audiovisual feedback system, in one aspect, comprises a self-hosted private cloud. In other aspects, the cloud-based audiovisual feedback system is applied to either a dedicated public cloud or, alternatively, a partner-hosted private cloud. Those of ordinary skill in the art will readily recognize any applicable cloud computing infrastructure for the cloud-based audiovisual feedback system.

In one further aspect, a health monitoring system connects with a health monitor that obtains a data sample from a participant. A data collection engine receives data from a data sample provided by a user, such as a blood sample, that is provided to the health monitoring system. A computer based audiovisual feedback system receives the data with the data collection engine and communicates with a feedback application engine, a data store, and a system controller. A feedback application engine can comprise of a gaming engine. The health monitoring system's output device, such as a display device, mobile device, social device, tablet, monitor, includes at least one processor and is capable of receiving signals from the gaming application and renders audio, visual, and other multimedia to the user. The output device is also capable of receiving input signals, for example through a touch screen. The user's feedback and other input signals are sent to an alteration engine that is capable to trigger a command to the system controller. The system controller provides a signal to the audio and visual display device, and warns the participant to manually control the rate of medication, for example, insulin, that is provided to the user. The system controller also communicates with the medical input testing system that is coupled to a medicinal injector, such as an insulin pump. The medicinal injector can inject the required dosage based on an interpretation factors such as the users emotional state, mood, medical state, or gaming inputs. Gaming inputs can include the amount of participating in the game, the game's analytic recommendations on dosage based on its interpretation of the user's game interactions, amount of time playing the game, questions that have been answered, or any other in game data point. In addition, the feedback application engine can associate the participant's data with a note or color and aggregate into a number of representations, such as a compilation of all notes that can be played or a compilation of colors that can be displayed. Furthermore, the visualization, sound compilation, or game can be displayed in a personal area network interactive display device.

A computer based audiovisual feedback system receives the data from the data collection engine and communicates with a feedback application engine, a data store, and a system controller. A feedback application engine can comprise of a gaming engine. In addition, the feedback application engine can associate the participant's data with a note or color and aggregate into a number of representations, such as a compilation of all notes that can be played or a compilation of colors that can be displayed. Furthermore, the visualization, sound compilation, or game can be displayed in a personal area network interactive display device The feedback application engine includes a display application. The display application receives the test input signal and generates a feedback audiovisual output signal based on the test input signal. Accordingly, in operation, each feedback audiovisual output signal is displayed on the output device, such as among others the corresponding audio and visual output displays of the output device used by the donating participant and, optionally, the plurality of participants. In one embodiment, the feedback application engine generates a continuous audio display and a continuous visual display by combining each consecutive feedback audiovisual signal received to form an electronic audiovisual playback file corresponding to the donating participant. The feedback application engine includes a display application that receives the test signal and generates a feedback audiovisual output signal based on the test signal. A data collection engine receives data from a data sample provided by a user, such as a blood sample, that is provided to the health monitoring system.

At times, as described herein for purposes of this disclosure and appended claims, the terms among others "Participant", "Participants", "Patients", "Diabetic", "Chronically Diseased", "Medical Facilities", "Physician", "Healthcare Professional", "Healthcare Administrator", "Billing Professional", "Heath Provider", "Pharmacist", "Combat Medic/Corpsman", "Information Technology Professional", "Technician", "Imaging Center", "Peer", "Administrator", "Originator", "Participant", "Node", "User", "User Agent Client", "Client", "User", "Petitioning User", "Requesting User", "Subscriber(s)" and "Source/Destination Endpoint" are used interchangeably for a logical network endpoint that transmits or receives Internet Protocol messages such as among others SIP messages through a user agent server. It is understood that "user" or "subscriber" refers to one or more operators of user equipment (UE). Those of ordinary skill in the art will readily recognize various embodiments of output devices or "UE", for purposes of illustration in this disclosure, the UE comprises either a wireless mobile device, such as among others a smart phone or tablet computer, or a wired device, such as among others a desktop computer, work station or a kiosk.

The users can be members of a "work request group", "group" or "talk group" that include a combination of preconfigured users, ad hoc users or members. Alternatively, subscribers may not be members of such groups. As described herein, a communication group in an audiovisual feedback system is referred to as a "network entity", "network entities", "network system", "network groups", "social network group" or "group". Accordingly, an audiovisual feedback system a plurality of network entities where it is possible for a user to be a member of any combination of groups and users.

Social networks are the relationships between individual members and groups within a given society. Criteria for inclusion may include possessing a specific skill or knowledge or having a certain personal attribute. Inasmuch, in this application the term a "social network" can be realized as a registry or catalogue of electronic information containing a listing of individuals bound by common skills, attributes or associations. Such a registry includes some information about each member of the registry. In this patent application, the term "Social Network refers" to a registry of participants to the health monitoring system within the field of chronic disease management that includes identification information about each participating member or "participant" such as, among others, a participant's name, contact information, geographic location, participant audio file catalog information, participant visual file catalog information, personal preferences as related to diabetes management, and optionally, current accepted provider or insurance network affiliations.

In this disclosure and appended claims the term "real time" "real-time" refers to denoting or relating to a computer system that constantly updates information at the same rate as the system receives data, and processes data sufficiently rapidly to be able to control a process. Accordingly, real time systems provided in this application refer to those that guarantee that the system will respond in a predetermined amount of time and that are used when an action must occur and a deadline by which we wish that action to take place so that the system must respond to changes and stimuli is a small and fixed period of time and in doing so provide notice of the change or stimulus to all participants.

In this disclosure and appended claims the term "data input" and "input" refers to data that is provided through user equipment to the cloud-based audiovisual feedback system. In particular, each user engages in a direct communication session with the audiovisual feedback system by way of any combination of output devices comprising hardware and software and/or firmware.

In this disclosure and appended claims, the terms "Protected Health Information, PHI", "electronic Protected Health Information, ePHI", "ePHI related data", "electronic health records", "medical information", "medical records", "private information", "patient medical file", "patient information", "health records", "health information", "health information technology" refer to health information that is protected by government regulations and industry standards, among other means for protection, and includes, among others security and privacy regulations, such regulations as, among others, the *Security Standards for the Protection of Electronic Protected Health Information* (the Security Rule) published Feb. 20, 2003 (45 C.F.R. Part 160 and Part 164, Subparts A and C) and established standards for protecting Health Information (ePHI) conveyed by electronic means (hence "ePHI") (hereinafter referred to as "the ePHI security rule"); the *Health Insurance Portability and Accountability Act* (hereafter "HIPAA") (Health Insurance Portability and Accountability Act of 1996 (HIPAA)); Public L. 104-191, 101 Stat. 1936, enacted Aug. 21, 1996, (see also the HIPAA Privacy Rule (See 45 C.F.R. § 164.530(c) (technical safeguards for ePHI)) and the HIPAA Security Rule (See 45 C.F.R §§ 164.308, 164.310, and 164.312 (technical safeguards for ePHI)) (HIPAA Privacy and Security Rules refer to regulations for protecting the privacy and security of health information as developed by the Secretary of the U.S. Department of Health and Human Services (HHS).)); and the *Health Information Technology for Economic and Clinical Health Act* (HITECH Act) § 13410(d) (see eg. Meaningful Use (of Health Information Technology) Proposed Final Rule March/2012 (addressing the privacy and security concerns of ePHI)); HITECH Act as part of the American Recovery and Reinvestment Act of 2009 (ARRA), Public L. 111-5, enacted Feb. 17, 2009 (hereinafter, collectively, referred to as "The HITECH Act"). In at least one embodiment, ePHI includes information associated with user identification and authorization. The term "security" includes common computer and security methods but also includes legally mandated health information privacy and security methods.

In this application and appended claims the term "network translation" includes among others Communications or Network Protocol translation, Data Protocol Translation, Data Organizational Protocol Translation and Security Protocol Translation Communications or Network Protocol Translation includes managing translation and distribution of network communications from a personal area network or "BLUETOOTH brand" network to fiber channel network; or an HTTP to an instant messaging protocol among other illustrations. This might include, among others, adding domain specific communications information such as destination addresses and error correction functionality to ensure a message is correctly forwarded from one network to another. Data Protocol Translation includes managing the translation of data to a common or requested format such as, among others, ASCII to compressed, compressed to ASCII, and jpeg to png. Data Organizational Protocol Translation includes managing the translation of data provided in a specific structure by a source to the structure required by the destination. Security Protocol Translation includes managing the addition of security features to messages to be communicated. This might involve adding, authenticating, encrypting or decrypting security addenda to packets to be communicated in a manner consistent with the overall system but transparent to the underlying communications, data or organizational protocols.

In this application and appended claims the term "header template", "template" allows a function application to work on many different data types without being rewritten for a user login session such that an arrangement of templates for each login session is provided, for example, at a data packet that includes a header template whereby the data packet defines, at least in part, a token. Those of ordinary skill in the art will readily recognize that other embodiments will use a "template" and "header template" for more than one login session.

In this application and appended claims the term "trigger" refers to an external stimulus that engages a functional response by the cloud-based audiovisual feedback system.

While embodiments of the present disclosure employ various teachings of the aforementioned standards and protocols, the embodiments as described herein are not limited by these protocols. Those skilled in the art will realize that the above recognized advantages and other advantages described herein are merely illustrative and are not meant to be a complete rendering of all of the advantages of the various embodiments.

Referring now to the figures, FIG. 1 generally illustrates a health monitoring system 10 for receiving a medical test sample from a donating participant 1 having a chronic disease of a plurality of such participants 1a. For purposes of illustration in this application, the health monitoring system 10 is applied to a glucose monitoring system 10 for example. Those of ordinary skill in the art will readily recognize other applications of the health monitoring system 10 to other chronic illnesses such as, among others, cancer, high blood pressure, heart disease, autoimmune diseases such as AIDs and arthritis, asthma, obesity, tobacco and alcohol use.

Accordingly, the blood glucose monitoring system 10 communicatively connects with a standard blood glucose meter 29 for receiving a medical test blood sample 22 from a donating participant 1 from a plurality of participants 1a. The blood glucose monitoring system 10 includes a medical testing input system 20, a computer-based audiovisual feedback system 50 and at least one output device 70.

In particular, the medical testing input system 20 is coupled to the standard blood glucose meter 29. Operatively, the blood glucose meter 29 receives the medical test blood sample 22 and provides a test output to the medical testing input system 20. The audiovisual feedback system 50 receives a test input signal from the medical testing input system 20. The medical testing input system 20 generates the test input signal based on the medical test blood sample 22.

The audiovisual feedback system 50 includes a registry archive 55 that is communicatively connected to the plurality of participants 1a, a feedback application engine 61 that is communicatively connected to the registry archive 55, an alteration engine 66 that is communicatively connected to the feedback application engine 61, and the registry archive 55, and a system controller 63 that is communicatively connected to the alteration engine 66, the feedback application engine 61, and the registry archive 55.

The feedback application engine 61 includes a display application. The display application receives the test input signal and generates a feedback audiovisual output signal based on the test input signal. Accordingly, in operation, each feedback audiovisual output signal is displayed on the output device 70, such as among others the corresponding audio and visual output displays 71', 81', 91' of the output device 70 used by the donating participant 1 and, optionally, the plurality of participants 1a. In one embodiment, the feedback application engine 61 generates a continuous audio display and a continuous visual display by combining each consecutive feedback audiovisual signal received to form an electronic audiovisual playback file corresponding to the donating participant 1.

With reference to the output devices 70, each output device 70 is communicatively connected to the computer-based audiovisual feedback system 50. As shown, the output devices 70 can be a mobile interface display device, 81, a social interactive display device 91, and a personal area network display device 71 (PANIDD). Generally, the at least one output device 70 receives the feedback audiovisual output signal and provides an audio and visual output display based on the test output of the donating participant 1.

The audio and visual output display is based on a continuity of predetermined musical tones and predetermined colors, respectively. Each tone and color corresponds to a predetermined physiological mental state or, commonly, physical "emotion" or "mood" experienced by the donating participant 1 at the time the medical test blood sample 22 is received by the medical testing input system 20 as a function of blood glucose level.

In operation, the donating participant 1 provides a feedback audiovisual input signal, based on the feedback audiovisual output signal, to the alternation engine 66, via the output device 70. The alteration engine 66, responsive to the feedback audiovisual input signal, generates a command signal to thereby trigger the system controller 63.

In one embodiment, the system controller 63 provides a controller signal, based on the command signal, to the audio and visual output display of the output device 70. The system controller 63 operates the output device 70 to warn the donating participant 1 to manually control the rate of medication provided to the donating participant via a responsive, second feedback audiovisual output signal having predetermined audiovisual alerting information.

The system controller 63 provides a controller signal, based on the command signal, to medical input testing system 20. As shown, the medial input testing system 20 is coupled to a medicinal injector 20'. The system controller 63 operates the medicinal injector 20' responsive to the controller signal to control the rate of medication provided to the donating participant 1 responsive to the feedback audiovisual input signal. In one embodiment, the medicinal injector 1 comprises an insulin pump.

The audiovisual feedback system 50 further includes a social application. The social application is communicatively coupled to the registry archives 55, the display application, the alteration engine 66, and the system controller 63. Operatively, another participant 1a from the plurality of participants 1a provides a feedback audiovisual input signal, responsive to the feedback audiovisual output signal of the donating participant, to the alternation engine 66, via the output device 70. Thus, the alteration engine 63, responsive to the feedback audiovisual input signal, generates a command signal to trigger the system controller 63 to control the rate of medication provided to the donating participant 1 responsive to the feedback audiovisual input signal of the another participant 1a.

In one exemplary embodiment, the audiovisual feedback system 50 further includes a gaming application that is communicatively coupled to the registry archives 55, display application, the alteration engine 66, and the system controller 63. With respect to the gaming application, the donating participant 1 and the plurality of participants 1a access the gaming application, based on a game generated by the gaming application. The gaming application generates a game controlled feedback audiovisual input signal, based on the game, to the alternation engine 66. The alteration engine generates a command signal to trigger the system controller 63 to control the rate of medication provided to the donating participant 1 responsive to the game controlled feedback audiovisual input signal.

Figure 21:
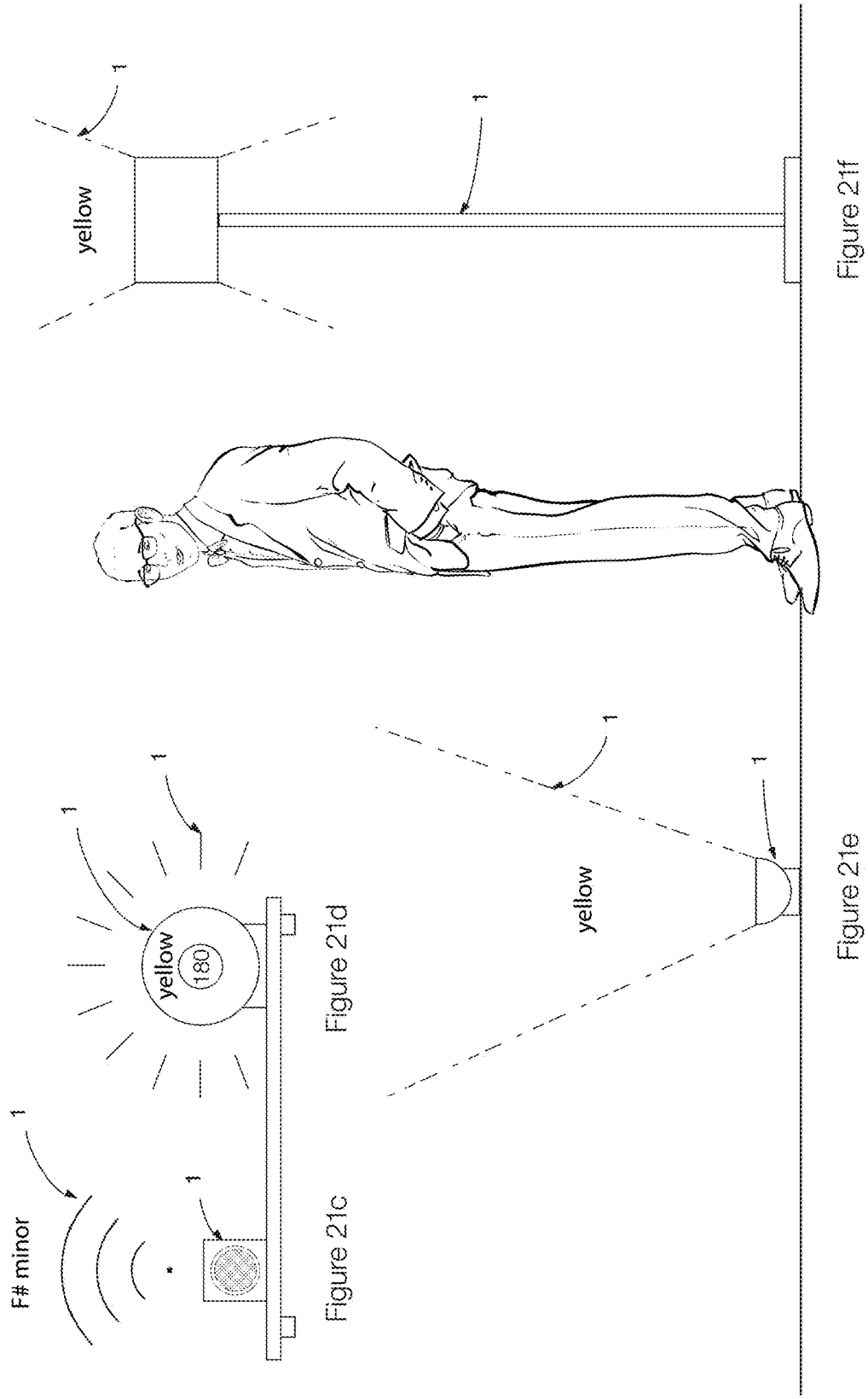
FIG. 21 is one exemplary embodiment of a game.
Figure 22:
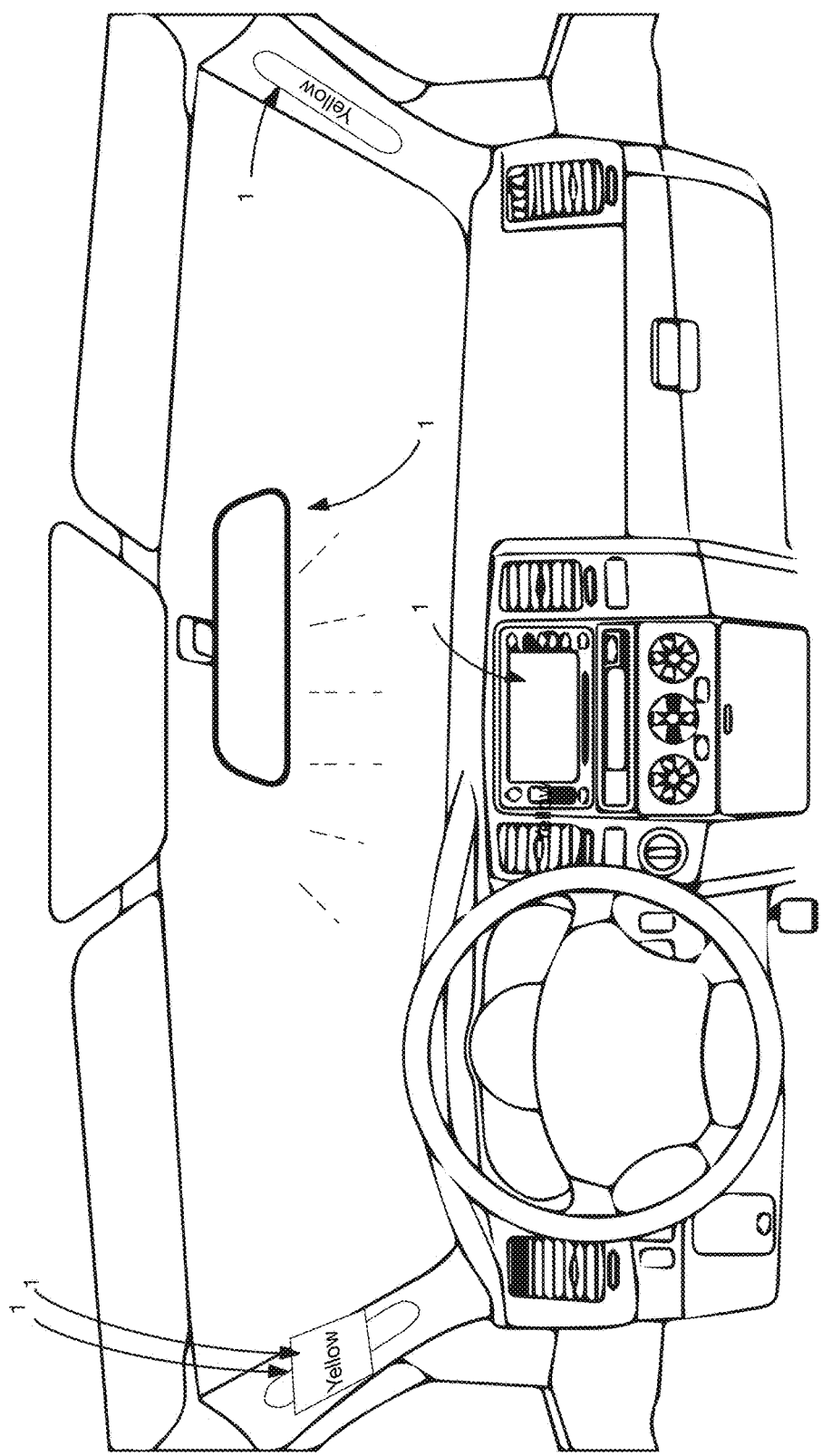
FIG. 22 is one exemplary embodiment of a game.

Game Example No. 1—GlucoCity Game:

Single Participant: With reference to FIGS. 21-23, construct a city 330 from a variety of historical and fictional settings with building materials dashboards 310 acquired by demonstrating good blood glucose levels. The 'city' 330 grows and evolves with contextual data such as time within a balanced glucose range. Users may move buildings around and make changes to them.

Optionally, with reference to FIG. 23, participants may activate a "chase" mode during game play to permit each participant to chase down a colored orb 333 quickly moving through the landscape 330 where the predetermined colors of the game's landscape indicate current glucose level of the donating participant 1. The participants listen to the blood sugar melodies 339 playing in the background to find the difficult-to-catch orb 333. During the course of the game, each time the orb 333 is caught changes the orb's 333 color within the game closer to a blue color, whereby the color blue is a predetermined color that represents a donating participant 1 with a desired, healthy blood glucose level. In one embodiment, the participant must catch the orb 333 multiple times to change the landscape 330 color to blue. As shown in FIG. 23, a social interactive display device 91 is gyrated 334 to assist movement of the orb 333 within the game play. Upon balancing the landscape to blue, the participant is transported to another landscape. Landscapes 330 represent blood sugar conditions, and the colored orb 333 represents either the addition of glucose or insulin to balance the blood sugar conditions. Optionally, the landscapes 330 can be those landscapes created by the above construct-a-city game exercise.

Companion Participants: Companions, i.e. the plurality of participants 1a on a social internet-based network, help primary users (the donating participant 1b), find the orb 333 by following the orb, whose melody's volume increases when touched by the helpful game companions.

Game Example No. 2—Balloon Game:

Gameplay: With reference to FIG. 24, a balloon 444 movement represents the changing blood glucose levels of the donating participant 1. For example, in FIG. 24a, a rising balloon represents increasing of blood glucose levels without medical intervention. In addition to teaching good self-administered health care practices to participants, the game optionally provides the ability to receive insulin or other medication as part of the game play. In operation, participants, such as the donating participant 1, holds and gyrates the mobile device 81 to guide the balloon 444 toward desired floating colored bubbles 445, see FIG. 24b. Referring to FIG. 24c, the balloon 444 is a tool used in the game to pop the colored bubble 445 from the opposite end of a predetermined blood glucose level color gradient in the attempt to return the colored balloon back to balanced blue that represents a donating participant with a desired, healthy blood glucose level. In one embodiment, the colored bubbles are derived from the donating participant's actual glucose history where each predetermined color represents a blood glucose reading. In another embodiment, the colors bubbles are randomly generated.

Illustratively, an exemplary method of dispensing insulin to a donating participant 1 from a plurality of participants 1a may be appreciated as follows. The method is implemented by one exemplary embodiment of a blood glucose monitoring system 10. The blood glucose monitoring system 10 includes an audiovisual feedback system 50 having a system controller 63 and a feedback application engine 61, having a display application that is communicatively connected to a data collection engine 163 and an alteration engine 66. The blood glucose monitoring system 10 further includes a medicinal injector 20' that is communicatively connected to the audiovisual feedback system 50 and an output device 70 that is communicatively connected to the audiovisual feedback system 50. As shown in FIG. 1, the output device 70 includes a mobile interactive display device 81, a social interactive display device 91, and a personal area network display device 71. The term "personal area network" in this specification and appended claims refers to a mobile device that at least in part operates on IEEE standard 802.5 protocols.

The feedback application engine 61 includes a display application. The display application receives the test input signal and generates a feedback audiovisual output signal based on the test input signal. In one embodiment, the feedback application engine 61 generates a continuous audio display and a continuous visual display by combining each consecutive feedback audiovisual signal received to form an electronic audiovisual playback file corresponding to the donating participant.

Referring now to the method of dispensing insulin, a game is generated by a gaming application and accessed by the donating participant 1 with the output device 70. The donating participant 1 interacts with the gaming application to regulate the participant's 1 blood glucose levels. In the exemplary method, the gaming application is provided by the feedback application engine 61 and communicatively connected to the data collection engine 163 as well as communicatively connected to the medicinal injector 21 via the audiovisual feedback system 50. Optionally, to collectively monitor the health of the donating participant 1, at least one participant of the plurality of participants 1a accesses a game generated by the gaming application for play by the plurality of participants 1a, via a plurality of corresponding output devices 70.

In operation, the system controller 63 warns and prompts the donating participant 1 during game play to provide a plurality of feedback audiovisual input signal to the output device 70 to interactively control the rate of medication provided to the donating participant 1. In one exemplary method, warning and prompting the donating participant 1 further includes the step of generating a game controlled audiovisual feedback signal with the game application provided by the feedback application engine 61, as the donating participant 1 encounters a trigger within the game play. In the exemplary method, the trigger acts as a warning during game play. The trigger is provided by the feedback application engine 61 based on electronic data received from the data collection engine 163. Each electronic trigger is based on electronic data based on the donating participant's 1 currently metered blood glucose level. Accordingly, in operation, the feedback application engine 61 receives the data and continuously modulates the level of insulin delivered by the medicinal injector 20 to keep the donating participant's 1 blood glucose levels within predetermined levels to ensure proper healthcare of the donating participant 1.

In one exemplary method, a continuous audio display and a continuous visual display is generated by the feedback application engine 61. Accordingly, the feedback application engine 61 combines combining each consecutive feedback audiovisual signal received to form an electronic audiovisual playback file corresponding to the donating participant 1. Optionally, as the donating participant 1 interacts with an interface 81' provided by a mobile interactive display device 81, the feedback application engine creates musical compositions electronic data files and visual display compositions electronic data files based on a series of test outputs, such as a blood glucose test, provided by the donating participant to the audiovisual feedback system.

Referring to the exemplary method, the game controlled feedback visual input signal is received by the alteration engine 66. The alteration engine 66 generates and sends a command signal to the system controller 63 to change the rate of medication provided to the donating participant 1, via a medicinal injector 20, responsive to the game controlled feedback audiovisual input signal. Optionally, prompting, the donating participant 1 is prompted by the feedback application engine 61 to confirm the change in the rate of medication provided to the donating participant by the system controller 63. With the option, game play can be paused, via the feedback application engine 61, prior to generating the command signal to change to rate of medication provided to the donating participant 1 to prohibit advancement in the gaming application until the donating participant 1 confirm the change in the rate of medication provided to the donating participant 1 by the system controller 63. The game controlled audio feedback signal is stored in memory at a registry archives 55 communicatively connected to the data collection engine 163.

In the exemplary method, the alteration engine 66 predicts the response time of the donating participant 1 and changing the duration of game play triggers from the gaming application based on the response time prediction. Optionally, the alteration engine 66 predicts the response time of the donating participant 1 and changing the frequency of game play triggers from the gaming application based on the response time prediction.

FIG. 1 is a system diagram featuring a health monitoring system 10 in accordance with embodiments of the present disclosure featuring a cloud-based audiovisual feedback system 50 for interfacing with a participant 1 donating a medical test sample 22 as part of treating that participant's 1 chronic disease and, optionally, a plurality of participants 1a invited by the donating participant 1 to provide feedback to the audiovisual feedback system 50 with respect to treating the donating patient's 1 chronic disease. The cloud-based audiovisual feedback system 50 features at least one Software as a Service (SaaS) application that electronically provides an audio and visual output display for receiving audio and visual feedback from the donating participant 1. A plurality of authorized participants 1a through a game or through electronic information input to encourage positive chronic disease treatment behavior of the donating participant 1. Accordingly, the audiovisual feedback system 50 provides a change in the rate of medication delivered to the donating participant.

As shown in FIG. 1, the audiovisual feedback system 50 includes a web frontend module and a web backend module. The web frontend module is layered to communicatively connect with both an SaaS module having the system controller 63, feedback application engine 61, alteration engine 66, PaaS tooling 68 and Paas Plugin 69 as well as the registry archives 55. The web frontend module includes a user interface 36 and an application programming interface, API, 32. Similarly, the web backend module is layered to communicatively connect with the SaaS among others. The web backend module includes an application programming interface 34 and a service delivery portal 38. Accordingly, in operation, the PaaS plugin 69 and tooling 68 facilitate operation of the functional applications, among other applications, provided by the audiovisual feedback system, via the service delivery portal 38, as applied to the at least one output devices 70, as shown. The web frontend module and the web backend module are each communicatively connected to at least one output device 70, such as mobile user equipment. The web frontend module and the web backend module are each communicatively connected to the at least the medical testing input system 20 and the medicinal injector 20'.

Moreover, to effectuate treatment of the patient in an emotionally stimulating, encouraging manner during the perpetual course of treating the associated chronic disease, an audiovisual playback file corresponding to the donating participant's 1 treatment over time in the form of a musical composition including a rhythm, melody, harmony and, optional lyrics, and a moving image composition featuring predetermined images such as colors, scenes, individuals and animals as well as objects, are each derived through interacting with the audiovisual feedback system 50.

Figure 2:
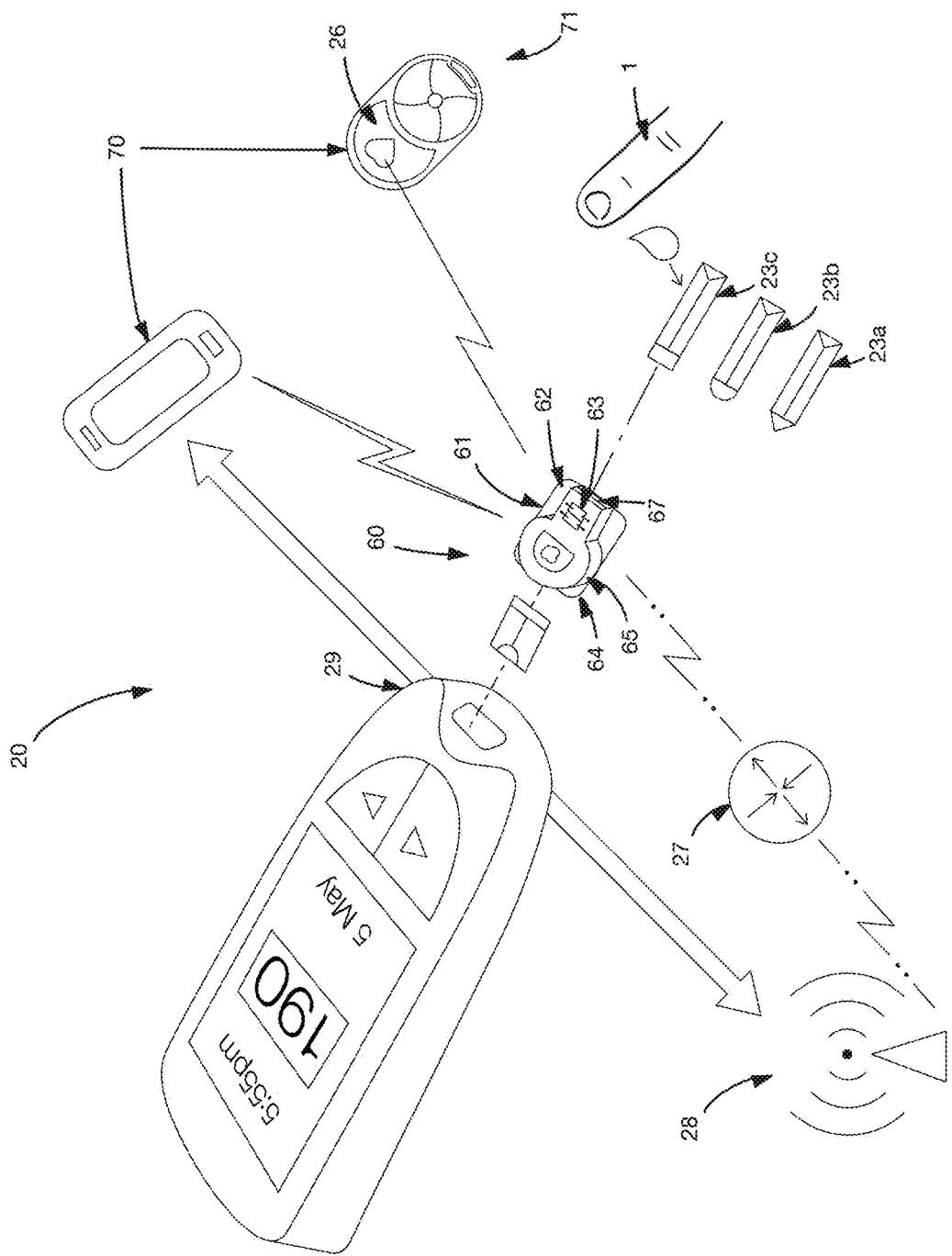
FIG. 2, is an isometric view of a medical testing input system for receiving a medical test sample, such as among others a blood sample, from a donating participant from a plurality of participants, the medical testing input system in one exemplary embodiment includes a standard blood glucose meter well known in the art (having a medical test receiving port for receiving standard test devices such as among others corresponding manufacturer blood test strips although those skilled in the art will readily recognize other metering devices for chronic illnesses) and an input collector system coupled to the standard blood glucose meter, the input collector system includes a gateway interface for insertion in the medical test receiving port and for operatively integrating the standard blood glucose meter with an audiovisual feedback system, the input system connector includes a receiver and transmitter for wireless networks including accessing radio access towers and commercial wireless cell phone caries and accessing personal area network networks such as BLUETOOTH brand enabled devices for audiovisual display and interactivity with the donating participant and, optionally, a plurality of authorized participants, illustratively a personal area network display from a output device illustrated as a personal area network interactive display device (PANIDD) is provided on the inside brim of a baseball hat or "ball cap" for audiovisual interactivity with the audiovisual feedback system.

FIG. 2, is an isometric view of a medical testing input system for 20 receiving a medical test sample 22, such as among others a blood sample, from a donating participant 1 of a plurality of participants 1a interacting with the health monitoring system 10. The medical testing input system 20, in one exemplary embodiment, includes a standard blood glucose meter 29 well known in the art (having a medical test receiving port 29a for receiving standard test devices 23 such as among others corresponding manufacturer blood test strips 23a, 23b, 23c although those skilled in the art will readily recognize other metering devices for chronic illnesses) and an input collector system 60 coupled to the standard blood glucose meter 29. The input collector system 60 includes a gateway interface 662 for insertion in the medical test receiving port 29a and for operatively integrating the standard blood glucose meter 29 with an audiovisual feedback system 50. The input collector system 60 includes a system connector 61 that defines a universal test receiver 67 for receiving standard test devices 23. The system collector 60 includes at least one fastening portion 64 to ensure that the input collector system 60 is coupled to the standard blood glucose monitor 29. In one embodiment, the system collector 61 is composed of silicone material. Optionally, the system collector 61 includes an audiovisual display 65 for interacting with at least one participant 1, 1a to the health monitoring system 10 in the manner described herein, for example audiovisually displaying electronic information derived by the audiovisual feedback system 50 from feedback audiovisual input and output signals. The registry archive 55 of the audiovisual feedback system 50 ensures the correct electronic display information is provided to the audiovisual display 65 and the output devices of the corresponding participant 1 or participants 1a. Moreover, ePHI, audio electronic data files, and visual electronic data files of the donating participant 1 and optionally plurality of participants 1a are accessed by the registry archive 55, via respective ePHI storage 42, audio data storage 44, and visual data storage 46, respectively.

In one illustrative embodiment, the input collector system 60 permits the standard blood glucose meter 29 to collect a medical test blood sample 22 from the donating participant 1, via the corresponding standard test device 23, such as a manufacturer glucose level test strip 23a. FIG. 2 shows exemplary configurations of test devices 23a, 23b, 23c provided by various manufacturers widely known in the industry.

Furthermore, the input collector system 60 receives the medical test blood sample 22, via the standard blood glucose meter 29, and generates a test output based on the medical test blood sample 22. The input collector system 60 transmits the test output to thus provide the test output to the computer-based audiovisual feedback system 50.

FIG. 2 shows various means for providing test output and, optionally, feedback audiovisual input signals to at least one output device 70. As shown, the medical testing input system 20 optionally includes a router 27 communicatively connected to a radio access tower network 28. Generally, FIG. 20 is a schematic diagram that shows mobile interactive display device 81 coupled to one embodiment of a medical testing input system 20, shown in FIG. 20a, having a housing 881, a universal test transceiver 67 integrated with the housing 881 and a gateway interface 62 for insertion into a receiving port 81a, shown in FIG. 20b.

The system connector 61 includes a receiver 62 and transmitter 63 for wireless networks including accessing radio access towers 28, commercial wireless cell phone carriers, and accessing personal area network networks 71, such as BLUETOOTH brand enabled devices for audiovisual display and interactivity with the donating participant 1 and, optionally, a plurality of authorized participants 1a. Illustratively a personal area network device provide by the at least one output device 70 is shown as a personal area network interactive display device (PANIDD) 71 that is specifically provided on the inside brim of a baseball hat or "ball cap" for audiovisual interactivity with the audiovisual feedback system 50.

In one exemplary embodiment, the PANIDD 71 is a gridded surface 199 mounted to the inside brim of the ball cap having an array 199a of predetermined color "swatch" indicia on the gridded PANNID 71 surface and a status display 199b mounted to the inside brim of the ball cap for audiovisually indicating the current blood glucose level of the donating participant 1. In one exemplary embodiment, the gridded surface 199 releasably couples to any surface. The array 199a and the status display 199b can each be coupled to separate surfaces from one another. Although in FIG. 1 the donating participant 1 is illustrated as wearing the ball cap, those of ordinary skill in the art will readily recognize at least one other participant of the plurality of participants 1a may wear an additional cap whereby each cap is networked with the computer-based audiovisual feedback system 50 for delivering medication to the donating participant 1. In one embodiment, the donating participant 1 must initially confirm delivery of medication by the medicinal injector 20'.

Correspondingly, a contact lens is applied to the eyeball of the donating participant 1 so that the spatial position of the cornea of the eye is monitored via electronic sensors to determine which predetermined color swatch that the donating participant 1 is directly looking at as a means for providing at least one other interactive feedback audiovisual input signal from the donating participant. In one exemplary embodiment each color is predetermined to indicate a physiological mental state or, commonly, physical "emotion" or "mood" that the donating participant 1 would like to achieve by engaging the controller to adjust the level of insulin, via a system controller 63, to a desired level based on the color swatch selected relative to the donating participants' 1 cornea directional position. In one embodiment, the spatial position of the cornea relative to the PANIDD 71's grid is determined by contact lens based sensors, where the contact lens comprises, among others, a smart contact lens by Google X of Mountain View, Calif. Accordingly, the PANNID 71 determines the location of the smart contact lens so that the audiovisual feedback system 50 interactively controls the rate of medication providing the donating participant 1 through manual delivery or via a medicinal injector 20'.

In an alternative embodiment, the spatial position of the cornea of a donating participant's 1 eye relative to the PANIDD 71's gridded surface 199 is by spatial sensors without a contact lens. In one exemplary embodiment, the spatial position of the cornea relative to the PANIDD 71's grid is determined by three-dimensional sensory monitoring of an eye ball's cornea within a spatial reference frame. In another embodiment, a feedback audiovisual input signal illustrated as a responsive visual input as sensory monitoring of an eye with infrared tracking of the lens of an eyeball relative to its retina relative to the output device, shown as a mobile interactive display device.

In operation, as the donating participant 1 selects the color swatch that will deliver enough medication, via the medical injector 20', to balance the current blood glucose level shown on the display that is also included on the hat brim. Although applied to a hat in the above illustration, those of ordinary skill in the art would readily recognize the gridded surface 199 having an array 199a of predetermined color "swatch" indicia and a status display 199b generally as input/output devices for the 50 for ubiquitous placement on objects to multiple settings. For example, among others, mounted to articles of clothing, shoes and accessories such as purses and scarfs; furniture; home decorative accents and lighting; pet collars, pet clothing as well as pet toys and pet accessories; lawn and garden equipment; home entertainment and consumer electronics equipment such as television and speakers; sports and outdoor equipment; and office supplies and equipment among others.

One exemplary embodiment of a blood glucose monitoring system 10 is appreciated as follows. Shown in FIG. 2, the blood glucose monitoring system 10 communicatively connects with a standard blood glucose meter 20 for receiving a medical test blood sample from a donating participant of a plurality of participants 1a. The blood glucose monitoring system 10 includes a medical testing input system 20, a computer-based audiovisual feedback system 50 and an at least one output device 70. The medical testing input system 20 is coupled to the standard blood glucose meter 29 via a gateway interface 662. The input collector system includes the gateway interface 662 for insertion in the medical test receiving port 29a and for operatively integrating the standard blood glucose meter 29 with an audiovisual feedback system 50. The blood glucose meter 29 receives the medical test blood sample and provides electronic data test output of the medical blood test sample to the medical testing input system 20. The medical testing system 20 receives the electronic data test output and generates a test signal based on the electronic data test output from the medical test blood sample.

The audiovisual feedback system 50 includes a registry archive 55 communicatively connected to the plurality of participants 1*a*, a feedback application engine 61 communicatively connected to the registry archive 55, an alteration engine 66 communicatively connected to the feedback application engine 61 and to the registry archive 55, and a system controller 63 communicatively connected to the alteration engine 66, to the feedback application engine 61, and to the registry archive 55. The audiovisual feedback system 61 receives the test signal from the medical testing input system 20. The feedback application engine 61 includes a display application that receives the test signal and generates a feedback audiovisual output signal based on the test signal.

The output device 70 is communicatively connected to the computer based audiovisual feedback system 50, and receives the feedback audiovisual output signal. The output device 70 provides an audio and visual output display based on the test output that corresponds to the blood glucose level of the donating participant at the time the blood sample was received by the blood glucose meter 29. The display of audio and visual output is based on a continuity of predetermined musical tones and predetermined colors, respectively. In one exemplary embodiment, each tone and color corresponds to a predetermined physiological emotional response diabetically experienced by the donating participant 1 for each test signal to audiovisually indicate the blood glucose level received by the medical testing input system 10 from the donating participant 1 and, optionally, from the plurality of participants 1*a*. The system controller 63 stores the another feedback audiovisual output signal in memory to predict the response time of the donating participant 1 and to change the frequency of warnings from the output device based on the response time prediction, via the alteration engine 66. The alteration engine 66, responsive to the feedback audiovisual input signal, generates a command signal to trigger the system controller 63 to control the rate of medication provided to the donating participant 1 responsive to the feedback audiovisual input signal of the another participant 1*a*. The system controller 63 operates the output device to warn the donating participant to interactively control the rate of medication provided to the donating participant 1 by prompting the donating participant 1 to respond to the warning by providing a feedback audiovisual input signal to the output device 70. Moreover, the system controller 63, responsive to another feedback audiovisual input signal, operates a medicinal injector 20' for controlling the rate of medication provided to the donating participant in response to the output device warning. In one exemplary embodiment, a feedback audiovisual input provides at least one musical note. In one exemplary embodiment, a feedback audiovisual input signal is derived from the eye movement of the donating participant 1. In one embodiment, the command signal includes a pause setting. In operation, the pause setting prohibits advancement in the gaming application until the donating participant 1 responsively medicates. In one exemplary embodiment, the feedback application engine 61 generates a continuous audio display and a continuous visual display by combining each consecutive feedback audiovisual signal received to form an electronic audiovisual playback file corresponding to the donating participant 1. In one embodiment, the output device includes a mobile interactive display device that includes an interface for a donating participant to make musical compositions and visual display compositions based on a series of test outputs, such as a blood glucose test, provided by the donating participant 1 to the audiovisual feedback system 50. The audiovisual feedback system 50 generates a template header. In one exemplary embodiment, the template header couples the musical and visual display compositions to the donating participant's 1 electronic medical records.

In one exemplary embodiment, as shown in FIG. 1, the audiovisual feedback system 50 further includes a feedback application engine that includes a gaming application, the social application communicatively coupled to the registry archives, and a display application. The audiovisual feedback system 50 further includes and the alteration engine and the system controller 63. In operation, the donating participant 1 and the plurality of participants 1*a* access the gaming application. Based on a game generated by the gaming application, the gaming application generates a game controlled feedback audiovisual input signal to the alternation engine 66. The alteration engine 66 generates a command signal to trigger the system controller to control the rate of medication provided to the donating participant 1 responsive to the game controlled feedback audiovisual input signal. As an option, the alteration engine 66, responsive to the feedback audiovisual input signal, generates a command signal to trigger the system controller 63 to control the rate of medication provided to the donating participant responsive to the feedback audiovisual input signal of the another participant 1*a*.

In another embodiment, a health monitoring system 10 may be appreciated. The health monitoring system 10 communicatively connects with a meter provided by the input collector system 60 for receiving a medical test sample from a donating participant 1 from a plurality of participants 1*a*. Generally, the health monitoring system 10 includes a medical testing input system 20, a computer-based audiovisual feedback system 50, and an output device 70.

The medical testing input system 20 is coupled to the meter, via a gateway interface 662. The meter receives the medical test sample and provides electronic data test output of the medical test sample to the medical testing input system 20. The medical testing input system receives the electronic data test output and generates a test signal based on the electronic data test output from the medical test sample.

The computer-based audiovisual feedback system 50 includes a registry archive 55 communicatively connected to the plurality of participants 1*a*, a feedback application engine 61 communicatively connected to the registry archive 55, an alteration engine communicatively 66 connected to the feedback application engine 61 and to the registry archive 55, and a system controller 63 communicatively connected to the alteration engine 66, to the feedback application engine 61, and to the registry archive 55.

The audiovisual feedback system 50 receives the test signal from the medical testing input system 20. The feedback application engine 61 includes a display application that receives the test signal and generates a feedback audiovisual output signal based on the test signal. Accordingly, the output device 70 receives the feedback audiovisual output signal and provides an audio and visual output display 71', 81', 91' based on the test output that corresponds to the metered level of the donating participant 1 at the time the medical test sample was received by the meter. The audio and visual output display 71', 81', 91' is based on a continuity of predetermined musical tones and predetermined colors, respectively, each tone and color corresponding to a predetermined physical emotion experienced by the donating participant for each test signal to audiovisually indicate the metered level received by the medical testing input system 20 to the donating participant 1 and, optionally, to the plurality of participants 1*a*.

The system controller 63 operates the output device 70 to warn the donating participant 1 to interactively control the rate of medication provided to the donating participant 1 by prompting the donating participant 1 to respond to the warning by providing another feedback audiovisual input signal to the output device 70. The system controller 60 operates a medicinal injector 20', responsive to the another feedback audiovisual input signal, for controlling the rate of medication provided to the donating participant 1 in response to the output device 70 warning.

In one embodiment for the above example, the output device 70 includes a personal area network device based on IEEE standard 802.15. The output device 70 includes a personal area network device 71 having an audio and visual output display 71' coupled to furniture. Optionally, the personal area network device 71 includes a gridded surface 199 releasably coupled to the furniture. In one illustration, furniture comprises a lamp for providing a visual display of the donating participant's 1 metered status and interacts with the donating participant 1 to control the rate of medication provided to the donating participant 1. In another illustration, household furniture comprises a speaker for providing an audio display of the donating participant's 1 metered status and interacts with the donating participant 1 to control the rate of medication provided to the donating participant 1.

Generally, FIG. 3 is a schematic diagram illustrating one exemplary embodiment of a mood display of a chronic disease sufferer 1 as related to the chemical levels of analyte that physiologically corresponds to the sufferer's clinical mental state or, commonly "mood" and "emotional" display as a function of time and their hypoglycemia. Specifically FIG. 3a shows one illustrative diagram of a diabetic's clinical metal state or "emotional" experience and resulting fatigue and emotional depression. FIG. 3b shows one illustrative diagram of a health monitoring system responsive to fatigue and depression experienced by the chronic disease sufferer 1.

Generally, FIG. 4, is a schematic diagram illustrating one exemplary embodiment of a mood display of a chronic disease sufferer 1 as related to the blood biochemistry state of hypoglycemia that physiologically corresponds to the sufferers experience as a clinical mental display as a function of time. Specifically, FIG. 4a shows one illustrative diagram of a diabetic's mental state or, commonly, "emotional" experience and resulting fatigue, emotional depression, and with difficulty breathing. FIG. 4b shows one illustrative diagram of a diabetic's "emotional" experience and resulting lack of concentration, irritability, and physiological display such as shakiness and sweating.

Figure 5:
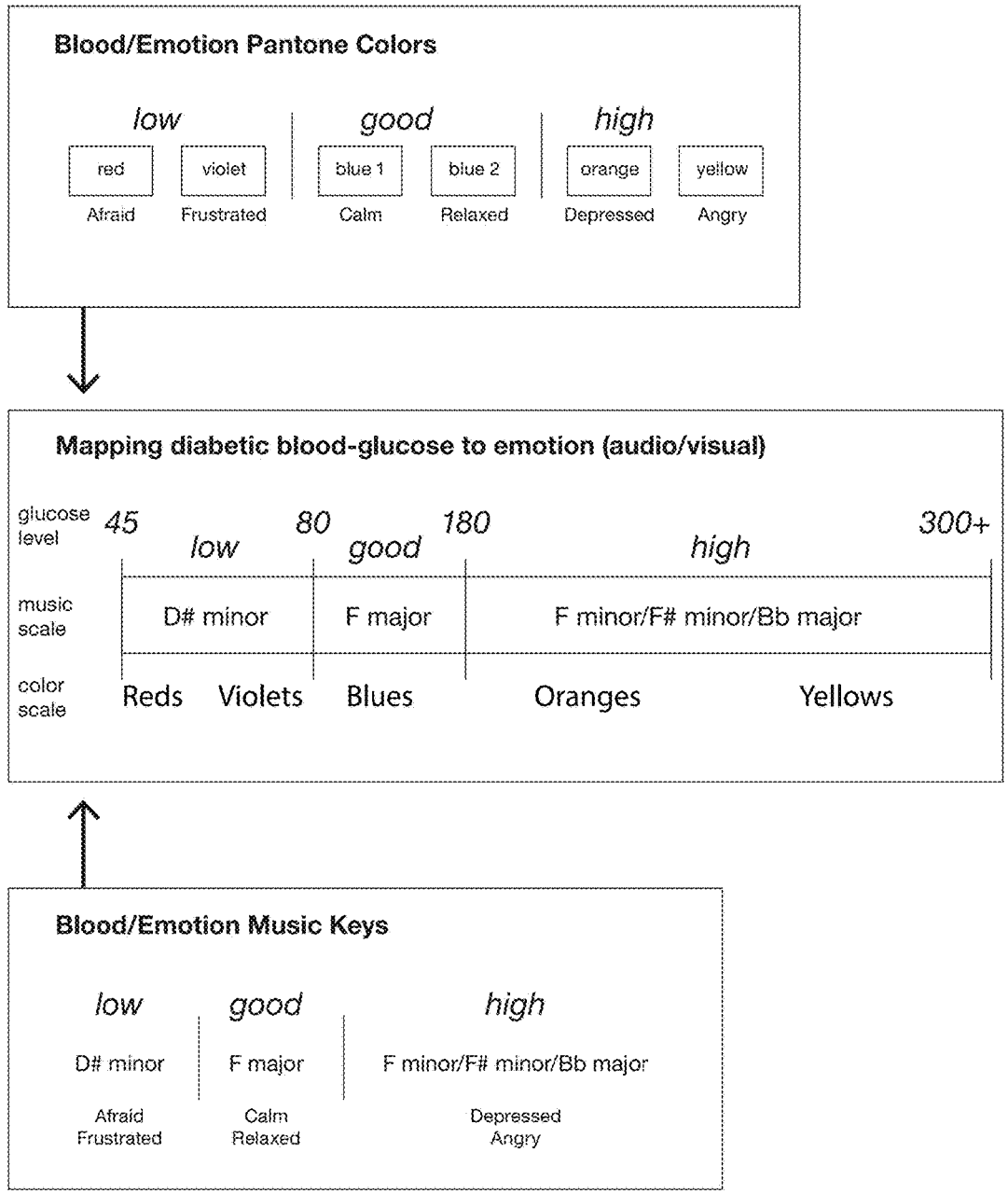
FIG. 5 is a schematic diagram illustrating one exemplary embodiment of a blood glucose level correlation with physiological mood with respect to a audiovisual feedback system of a health monitoring system; specifically

Generally, FIG. 5 is a schematic diagram illustrating one exemplary embodiment of a blood glucose level correlation with a donating participant's state of mind or, commonly, "mood" with respect to an audiovisual feedback system 50 of a health monitoring system 10. FIG. 5a illustrates one exemplary embodiment of predetermined color assignment to blood glucose correlation with a donating participant's state of mind or, commonly "mood" for use by the audiovisual feedback system 50. FIG. 5b illustrates one exemplary embodiment of predetermined musical keys assignment to blood glucose correlation with a donating participant's state of mind or, commonly "mood" for use by the audiovisual feedback system 50. FIG. 5c illustrates one exemplary embodiment of predetermined color assignment and predetermined musical keys assignment to blood glucose correlation with a donating participant's 1 state of mind that is subject to a chronic disease for use by the audiovisual feedback system 50.

Figure 6:
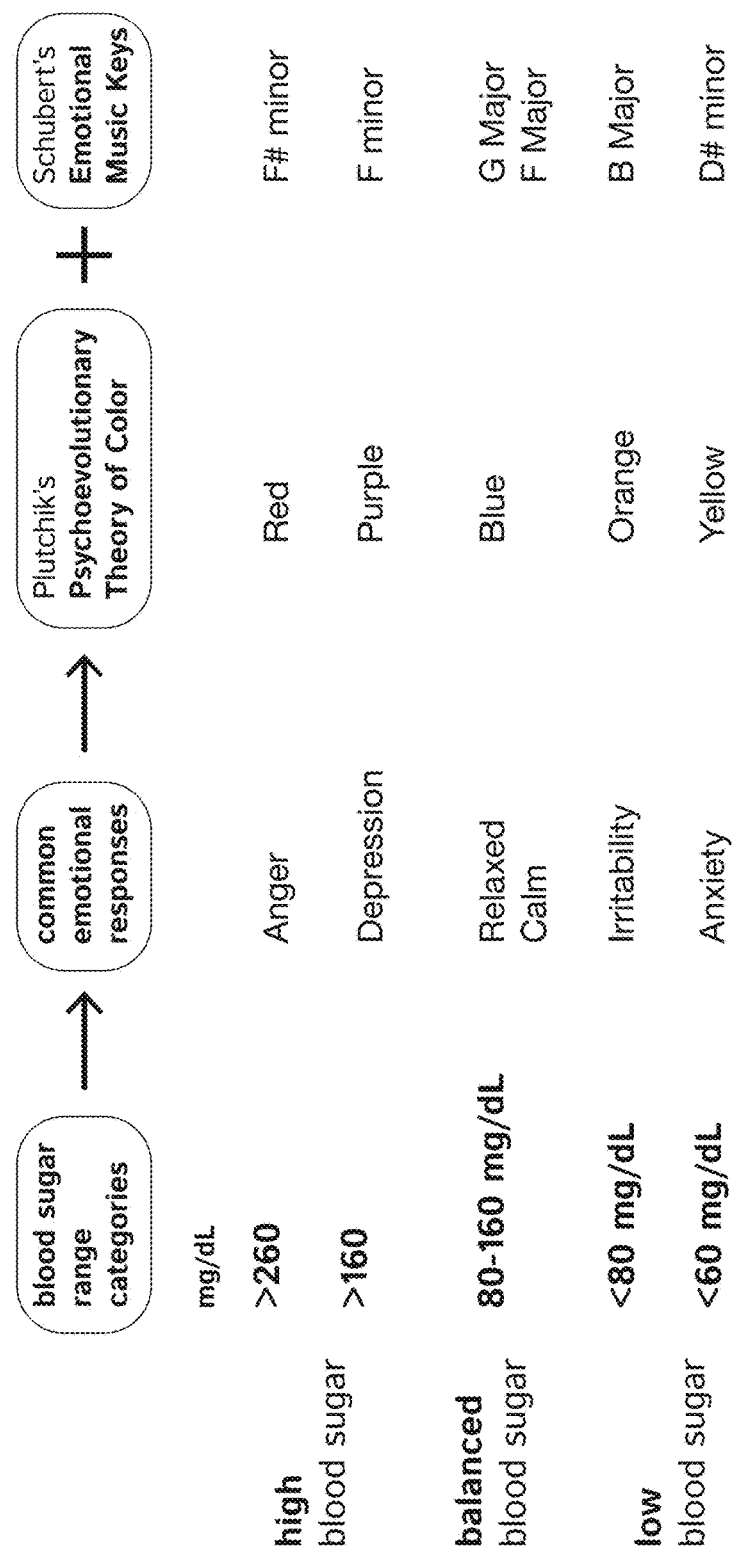
FIG. 6 is a schematic diagram illustrating one exemplary embodiment of a blood glucose level correlation with physiological emotion with respect to an audiovisual feedback system of a health monitoring system, and in particular.

Generally, FIG. 6 is a schematic diagram illustrating one exemplary embodiment of a blood glucose level correlation with a donating participant's state of mind with respect to an audiovisual feedback system 50 of a health monitoring system 10. In particular, FIG. 6 shows both a predetermined color assignment and a predetermined musical keys assignment to blood glucose correlation with physiological mood for use by the audiovisual feedback system 50.

Figure 7:
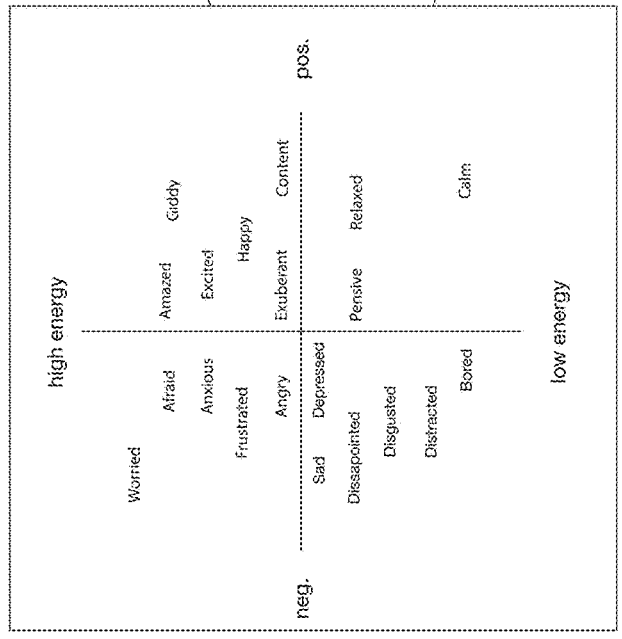
FIG. 7 is a schematic diagram illustrating one exemplary embodiment of a blood glucose level correlation with physiological emotion with respect to an audiovisual feedback system of a health monitoring system, and in particular.

Generally, FIG. 7 is a schematic diagram illustrating one exemplary embodiment of a blood glucose level correlation with a participant's 1 mental state with respect to an audiovisual feedback system 50 of a health monitoring system 10. In particular, FIG. 7a shows a board display that illustratively plots the donating participant's 1 mental state or, commonly, "emotional" levels attributed from ongoing hypoglycemia. FIG. 7b shows predetermined colors that are mapped to the board display of FIG. 7a attributable to the mental states of the chronically ill donating participant 1. FIG. 7c illustrates predetermined musical notes that are mapped to the board display of FIG. 7a. In one exemplary embodiment the board display is displayed as audiovisual information on at least one output device, such as the inside brim of a baseball cap of a PANIDD 71.

Figure 8:
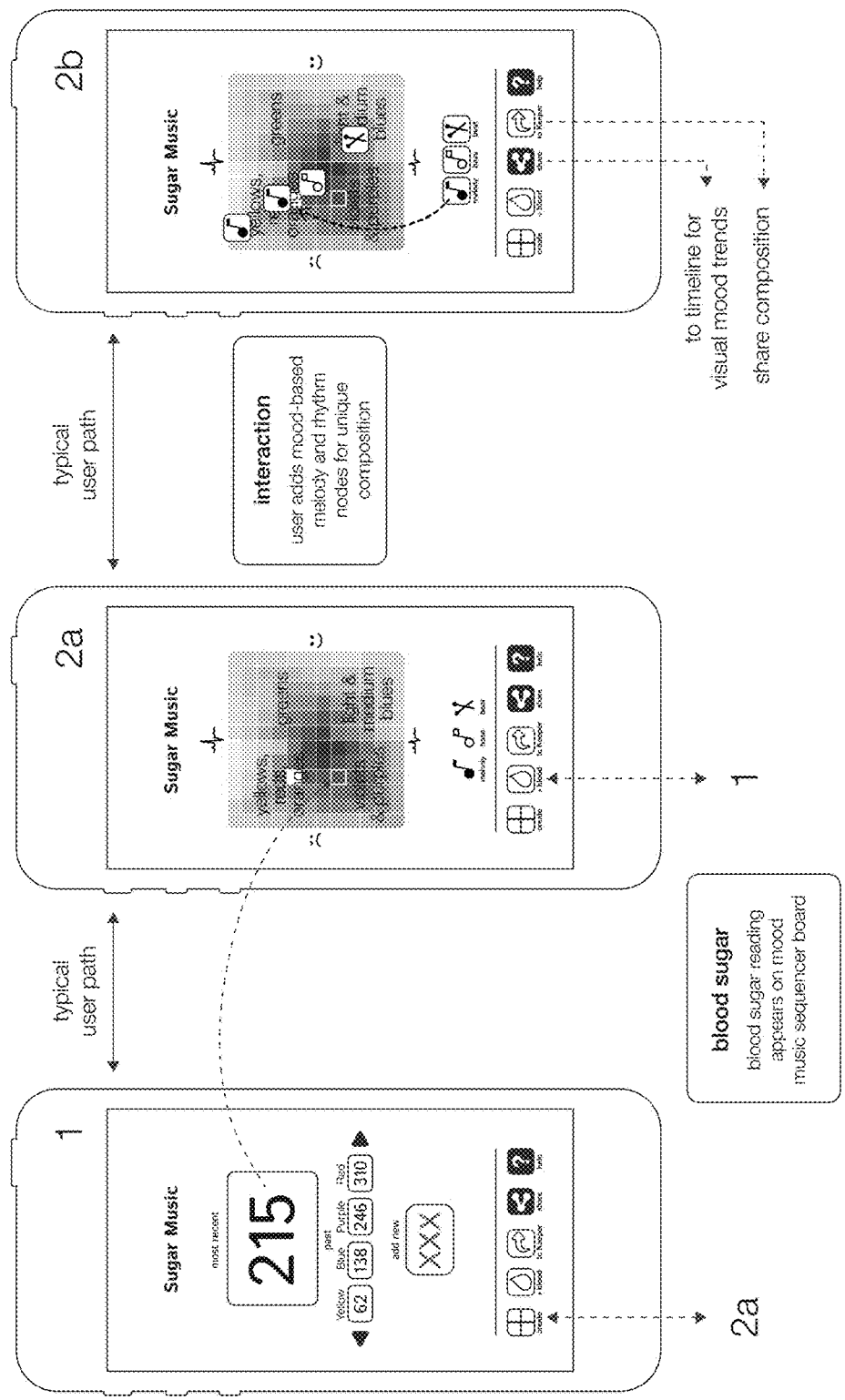
FIG. 8 is a schematic flow diagram illustrating one exemplary embodiment of operations of an audiovisual feedback system as applied to a mobile interactive display device.

FIG. 8 is a schematic flow diagram illustrating one exemplary embodiment of operations of an audiovisual feedback system 50 as applied to a mobile interactive display device 81.

Figure 9:
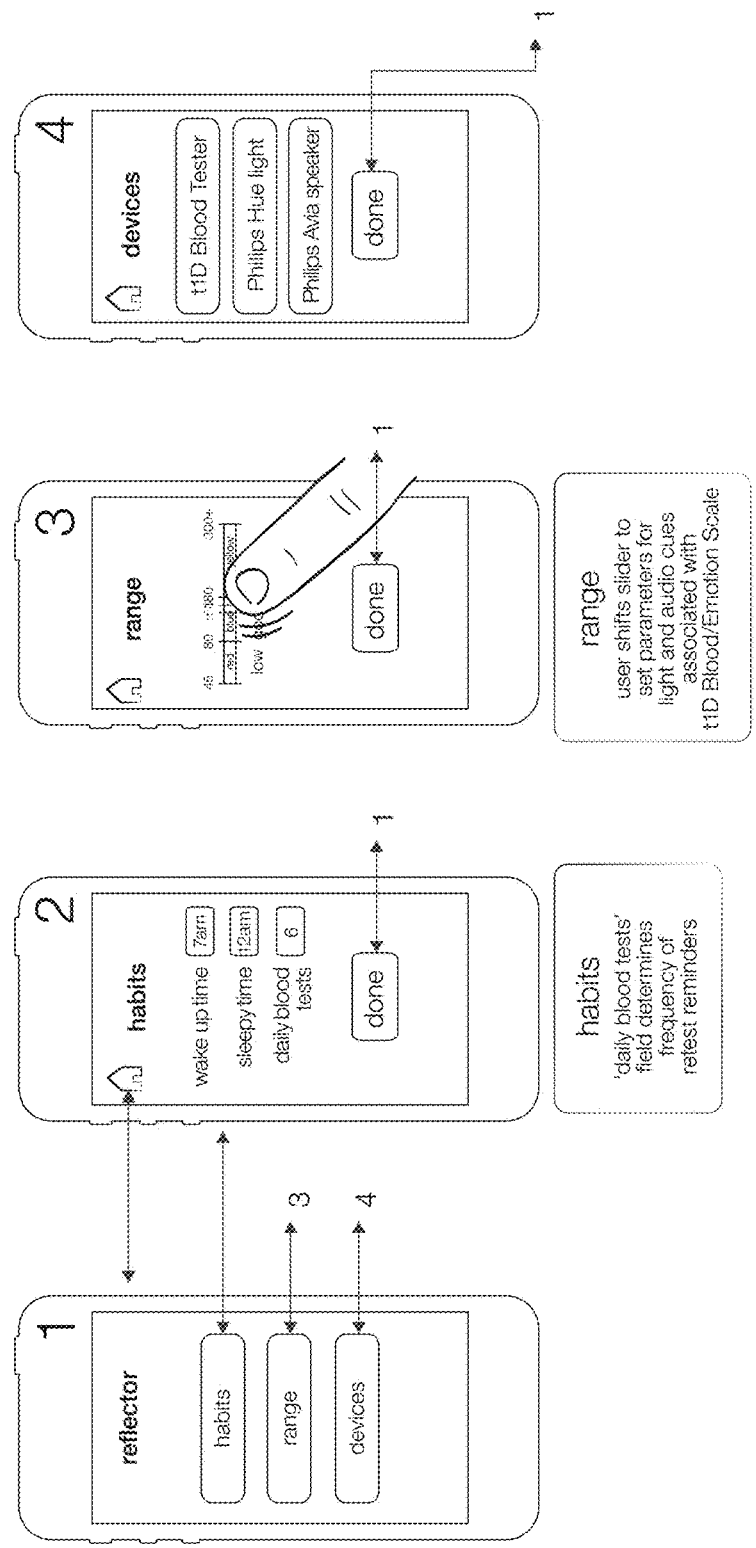
FIG. 9 is a schematic sequence diagram showing one exemplary embodiment of operations of an audiovisual feedback system as applied to a mobile interactive display device that illustrates one illustrative method for feedback application by at least one participant.

FIG. 9 is a schematic sequence diagram showing one exemplary embodiment of operations of an audiovisual feedback system 50 as applied to a mobile interactive display device 81 that illustrates one illustrative method for feedback application by at least one participant 1.

Generally, FIG. 10 is a schematic flow diagram showing one exemplary embodiment of operations of an audiovisual feedback system 50 as applied to a mobile interactive display device 81 that illustrates one illustrative method for feedback application by at least one participant 1. Specifically, FIG. 10a illustrates an operational flow of the audiovisual feedback system 50, via a mobile interactive display device 81, for a donating participant to make musical compositions and visual display compositions based on a series of test outputs, such as a blood glucose test, provided by the donating participant 1 to the audiovisual feedback system 50. FIG. 10b illustrates an operational flow of the audiovisual feedback system 50 for incorporating the donating participant's 1 musical compositions and visual display compositions as ePHI into a corresponding physician's electronic medical record ("EMR") that serves as the donating participant's electronic medical chart. FIG. 10c illustrates operational flow of the audiovisual feedback system for receiving, at least in part, a feedback audiovisual input signal from the eye movement of the donating participant 1 (as also shown in FIG. 11).

Specifically, with reference to FIGS. 10b and 19c, the donating participant's 1 musical compositions and visual display compositions are each electronic data packets generated by the audiovisual feedback system 50. Each electronic data packet includes a header template to permit each musical composition data packet or visual display data packet to compatibly integrate with any corresponding physician's EMR so as to become appended to the donating participant's electronic medical chart or records. In particular, the header template receives electronic data input from the corresponding physician's specific EMR system required for coupling the musical compositions and the visual display compositions to the patients existing EMR file. Accordingly, the header template provides interoperatibly with a variety of EMR systems well known in the industry.

In operation, at a subsequent visit with the corresponding doctor, the donating participant 1 reviews at least one musical composition or visual display composition to gauge progress of such medical treatment. In one exemplary embodiment, the at least one musical composition or visual display composition is reviewed as an attachment to the donating participant's EMR as displayed on mobile devices of a type well known in the telemedicine industry used by the corresponding physician's office.

Figure 11:
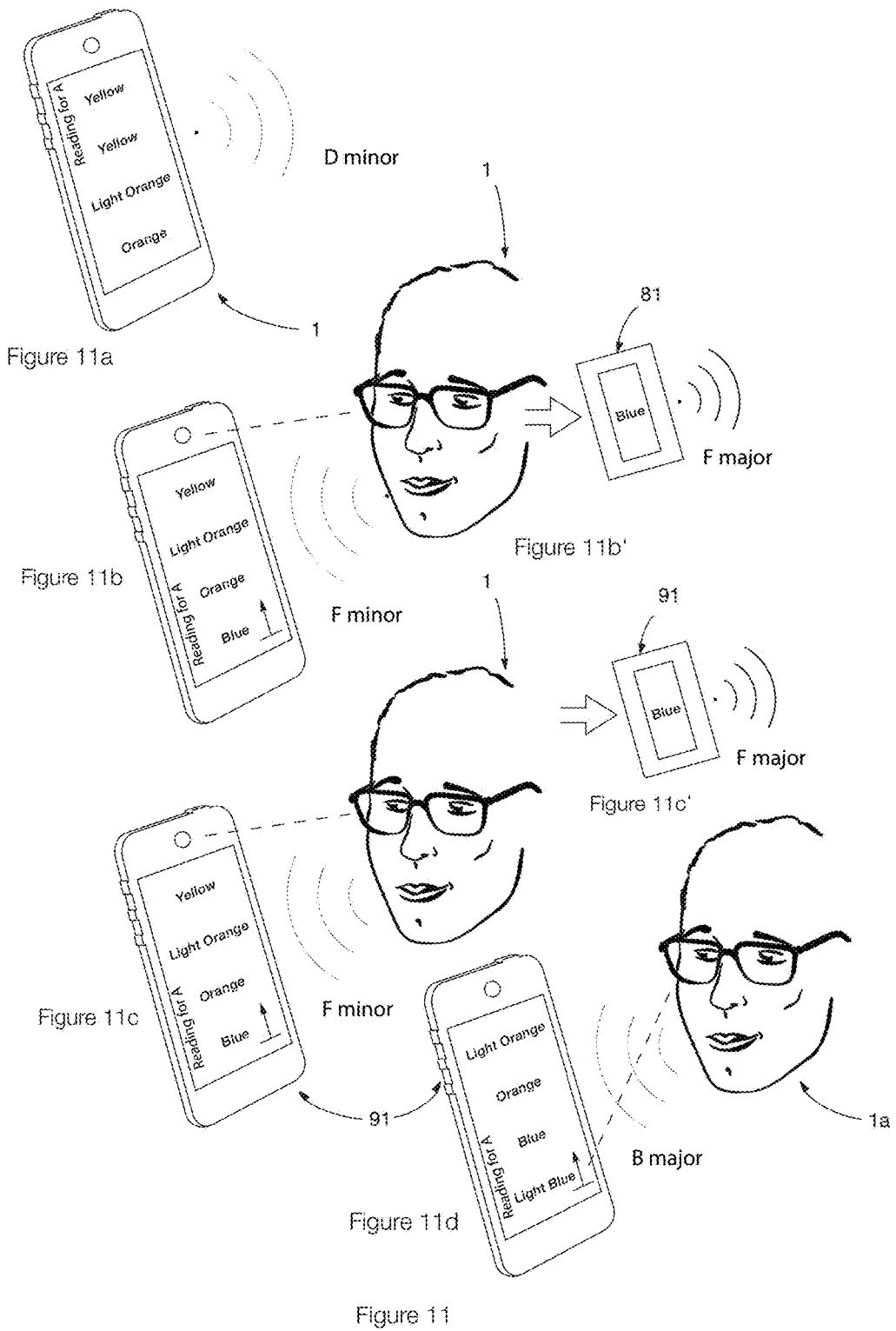
FIG. 11 is a schematic diagram illustrating exemplary operations of an audiovisual feedback system, via at least one output device, providing exemplary methods for providing feedback audiovisual input signals to the audiovisual feedback system in response to at least one participant receiving a corresponding feedback audiovisual output signal, in particular.

Generally, FIG. 11 is a schematic diagram illustrating exemplary operations of an audiovisual feedback system 50, via at least one output device 70. FIG. 11 provides exemplary methods for providing feedback audiovisual input signals to the audiovisual feedback system 50 in response to at least one participant 1 receiving a corresponding feedback audiovisual output signal. In particular, FIG. 11a shows the audiovisual feedback system 50 providing feedback audiovisual output signals including a donating participant's 1 musical compositions and visual display compositions to a mobile interactive display device 81. FIG. 11b shows an audiovisual feedback system 50 receiving, at a mobile interactive display device 81, a feedback audiovisual input signal, illustrated as a responsive audio F Minor input, from the donating participant 1 and a feedback audiovisual input signal, illustrated as a responsive visual input as retinal movement (to select a responsive predetermined color) relative to the output device 70, shown as a mobile interactive display device 81. FIG. 11b' shows a second feedback audiovisual output signal responsive to a trigger arising from receipt of the feedback audiovisual input signal to thereby increase the level of insulin of the donating participant 1 in response to the feedback audiovisual signal received by the donating participant 1. In one exemplary embodiment, the second feedback audiovisual output signal is illustrated as an F major musical key in the continuing musical composition of the donating participant 1.

FIG. 11c shows an audiovisual feedback system receiving, at a plurality of mobile interactive display devices 91, a plurality of feedback audiovisual input signals. Illustratively, the plurality of feedback audiovisual signals include a responsive audio F Minor input from the donating participant 1 and a feedback audiovisual input signal illustrated as a responsive visual input as corneal movement (to select a responsive predetermined color) relative to the output device and as a responsive B major input from another participant 1a from the plurality of participants 1a authorized by the donating participant 1 in compliance with government regulations regarding ePHI to participate in the donating participant's 1 treatment. FIG. 11c' shows a second feedback audiovisual output signal in responsive to a trigger arising from receipt of the feedback audiovisual input signals from both the donating participant 1 and another authorized participant 1a as shown. Illustratively, the second feedback audiovisual output signal shown in FIG. 11c' as a F major musical key in the continuing musical composition of the donating participant 1 to thereby increase the level of insulin of the donating participant 1 in response to the feedback input audiovisual signal received by the donating participant 1.

Figure 12:
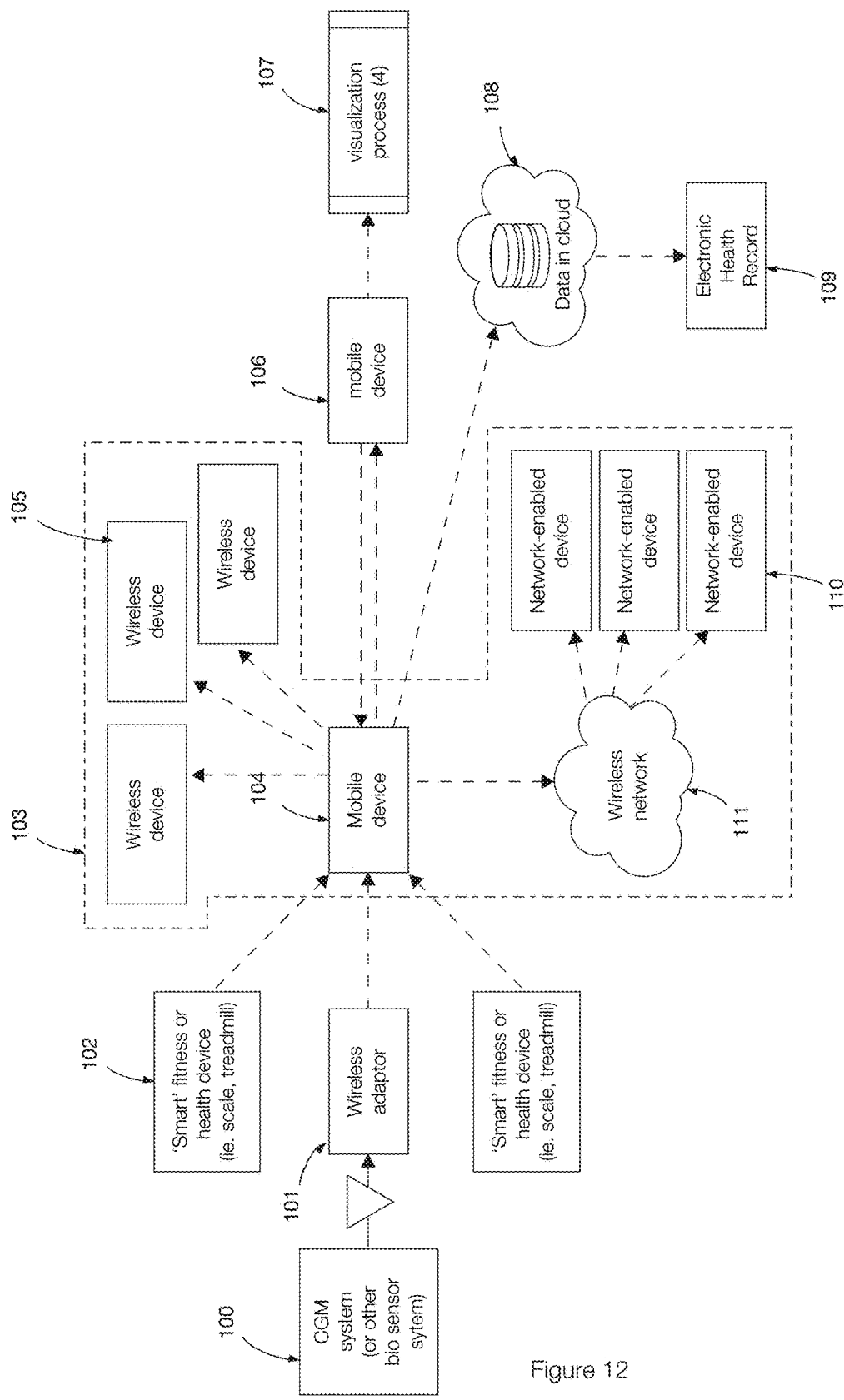
FIG. 12 is a schematic diagram of one exemplary embodiment of a mobile interactive display output device integrated with a smart home wireless network system having plurality of wireless network enabled devices and integrated with internet of things wearable devices for health monitoring.

FIG. 12 is a schematic diagram of a mobile interactive display 81 output device 70 integrated with a smart home wireless network system 202 having plurality of wireless network enabled devices 203, such as among others lamps, refrigerators, sofas, home theater systems and integrated with internet of things wearable devices 204 for health monitoring, such as among others a wearable pulse oximeter and blood pressure monitor.

Figure 13A:
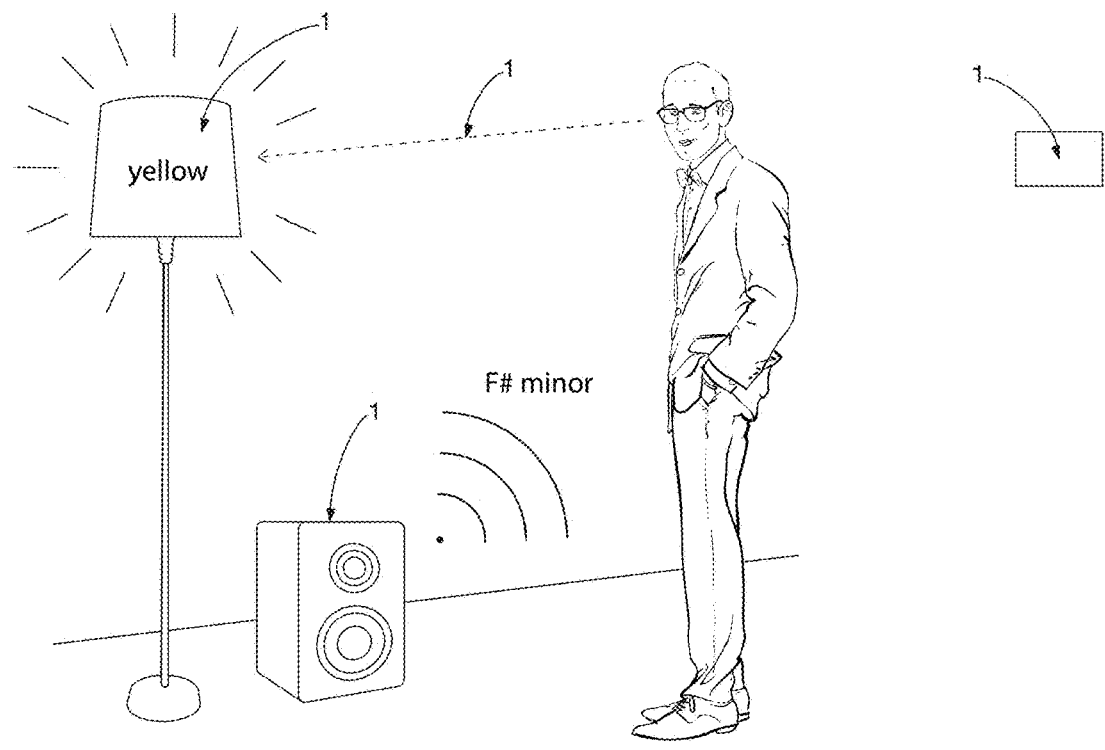
FIG. 13 is a schematic diagram illustrating one exemplary embodiment of a donating participant interacting with a personal area network interactive display device of a health monitoring system 10, specifically, in FIG. 13a, the donating participant receives a feedback audiovisual output signal to change their medicinal intake, and in FIG. 13b, the donating participant provides a plurality of feedback input audiovisual signals to a gridded surface mounted to the wall of the donating participant's office space including an array of predetermined color "swatch" indicia on the gridded surface and a status display.
Figure 13B:
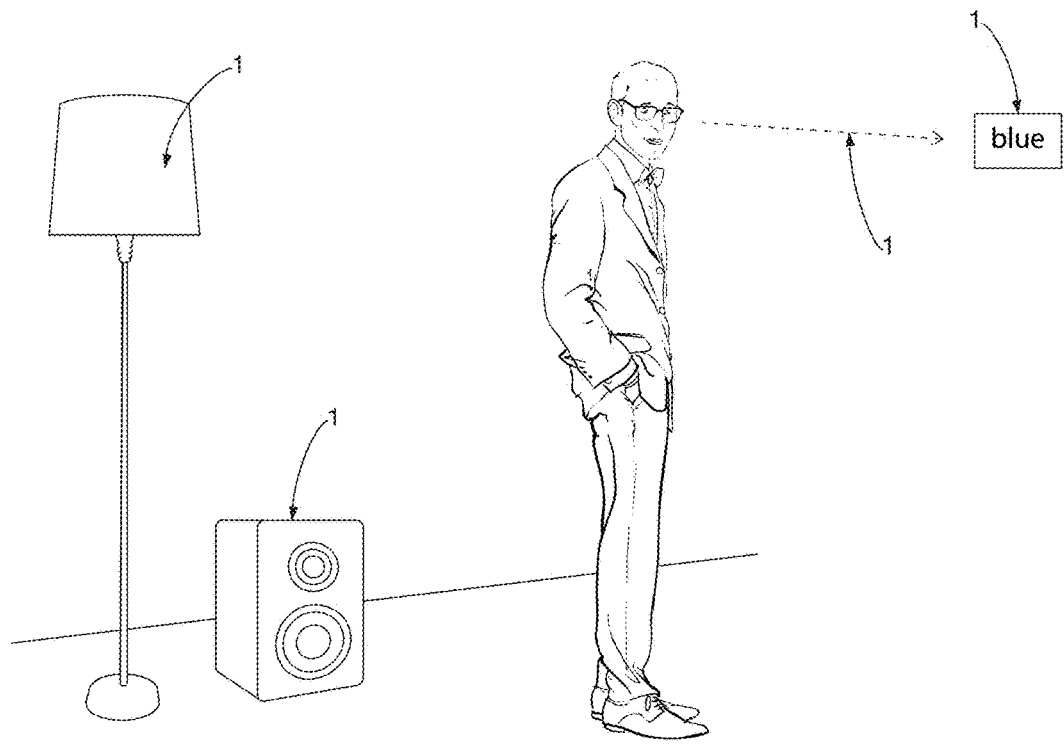

Generally, FIG. 13 is a schematic diagram illustrating one exemplary embodiment of a donating participant 1 interacting with a personal area network interactive display device 71 of a health monitoring system 10. Specifically, in FIG. 13a, the donating participant 1 receives a feedback audiovisual output signal 210, illustratively shown as a lamp changing to a yellow color and a f-minor chord from a speaker, indicating the donating participant 1 to change their medicinal intake. In FIG. 13b, the donating participant 1 provides a plurality of feedback input audiovisual signals 211 to a gridded surface 199 mounted to the wall of the donating participant's 1 office space. The gridded surface 199 including an array 199a of predetermined color "swatch" indicia on the gridded surface and a status display. The plurality of feedback input audiovisual signals 211 are shown as a visual selection of a predetermined color blue on the gridded surface 199 and a b-sharp melody with the lyrics of "increase" for receipt by the gridded surface 199.

FIG. 14 is a schematic diagram illustrating one exemplary embodiment of a donating participant 1 interacting with at least one personal area network interactive display device 71 of a health monitoring system 10. Specifically, a table and a sofa are each shown as an individual personal area network interactive display device 71, each having at least one gridded surface 199 integrated thereto. In FIG. 14, at least one a feedback audiovisual output signals 210 are emitted from the side of the table and from the armrests and underside of the sofa chair as shown.

FIG. 15 is a schematic diagram illustrating one exemplary embodiment of a donating participant 1 interacting with a plurality of output devices 70, 70a of a health monitoring system 10. In FIG. 15, at least one a feedback audiovisual output signals 210 are emitted from a wireless speaker, a lamp, an unmanned ground vehicle (shown adjacent to the donating participant's 1 feet, and a social output device 70a featuring a social interactive display device 91. In operation, the donating participant 1 interacts with the plurality of participants 1a through the social output device 70a.

Figure 16:
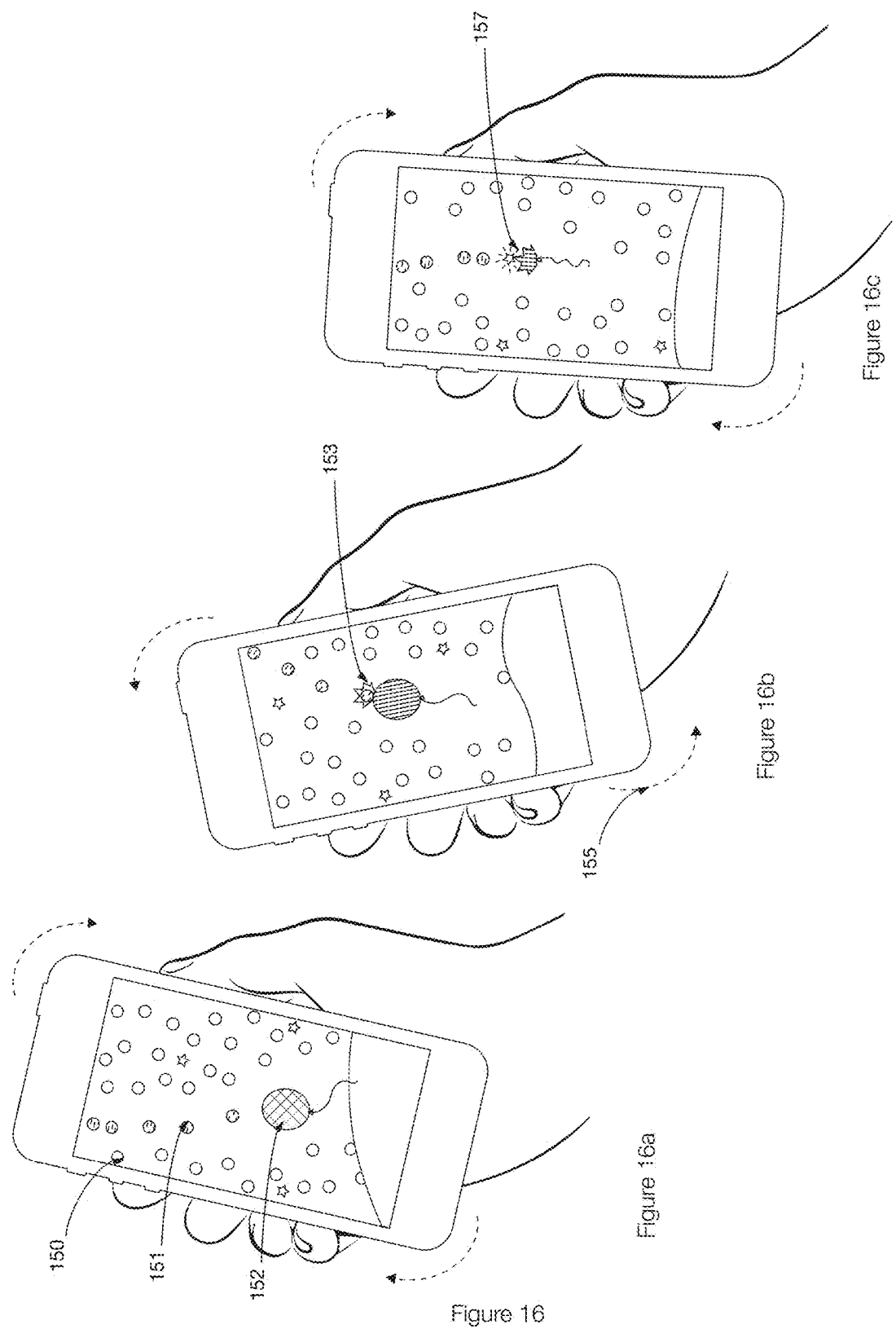

FIG. 16 and FIG. 17 illustrate different embodiments of a social output device 70a of FIG. 15. For the embodiment of FIG. 16, the social output device 70a includes a clear housing 220, audio speaker and microphone 221 and visual indicator display 222. For the embodiment of FIG. 17, the social output device 70a includes a clear housing 220, audio speaker and microphone 221 and audio indicator display 222.

FIG. 16a is a cross-sectional view of the social output device 70a of FIG. 16 such that within the clear housing 220 are a plurality of multicolored LEDs 225 that are connected by a network 224 to a processor 226. In operation, leds 225 of at least one shared predetermined color are illuminated in response to the donating participant's 1 blood glucose level.

Similarly, FIG. 17a is a cross-sectional view of the social output device 70a of FIG. 17 such that within the clear housing 220 are a plurality of multicolored LEDs 225 that are connected by a network to a microcontroller processor 223. In operation, leds 225 of at least one shared predetermined color are illuminated in response to the donating participant's 1 blood glucose level and a speaker 222a permits the plurality of participants 1a to interact with the donating participant via the microcontroller processor 223.

Figure 18:
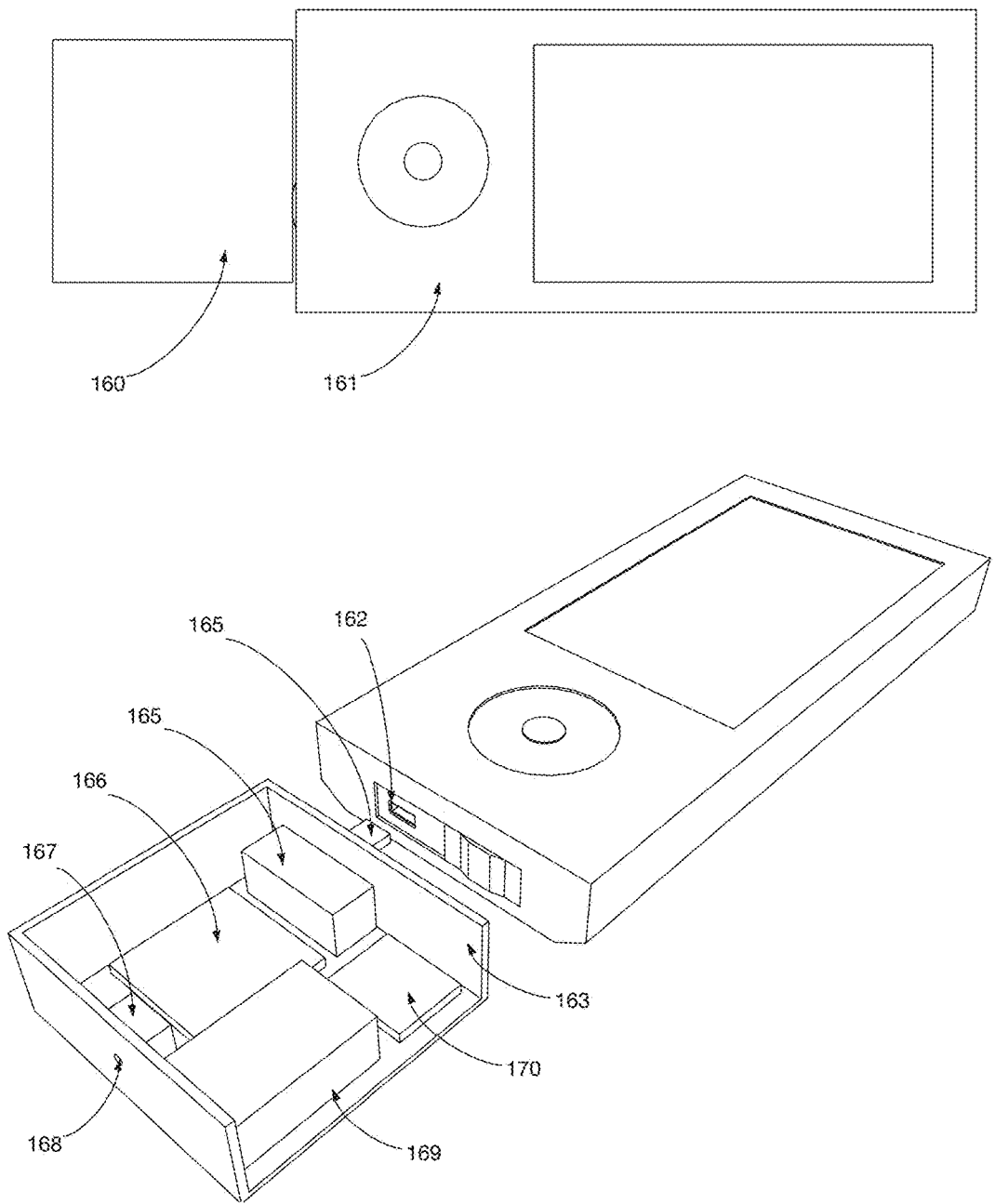
FIG. 18 is a schematic of a plurality of gridded surface interfaces of a health monitoring system that are integrated with a transportation device as shown.

FIG. 18 is a schematic of a plurality of gridded surface 199 interfaces of a health monitoring system 10 that are integrated with a transportation device 240 as shown.

Generally, FIG. 19 is a schematic diagram illustrating one exemplary embodiment of a donating participant interacting with a mobile interactive display device 81 of a health monitoring system 10, specifically, in FIG. 19a, the donating participant 1a receives a feedback audiovisual output signal 210 to change their medicinal intake. Moreover, for the embodiment of FIG. 19a, the mobile interactive display device 81 is shown as vibrating 219 to alert the donating participant 1. In FIG. 19b, the donating participant 1 provides a plurality of feedback input audiovisual signals 211 to the mobile interactive display device 81. In the embodiment of FIG. 19b at least one feedback input audiovisual signal of the plurality of feedback input audiovisual signals 211 comprises a song as shown. In FIG. 19c, the donating participant 1 provides a plurality of feedback input audiovisual signals 211 to the mobile interactive display device 81. In the embodiment of FIG. 19c at least one feedback input audiovisual signal of the plurality of feedback input audiovisual signals 211 comprises a song and visual interaction with the mobile interactive display device 81 as shown.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The terms "coupled" and "linked" as used herein is defined as connected, although not necessarily directly and not necessarily mechanically. A device or structure that is "configured" in a certain way is configured in at least that way, but may also be configured in ways that are not listed.

Also, the sequence of steps in a flow diagram or elements in the claims, even when preceded by a letter does not imply or require that sequence.

I claim:

1. A blood glucose monitoring system, the blood glucose monitoring system communicatively connects with a standard blood glucose meter for receiving a medical test blood sample from a donating participant of a plurality of participants, the blood glucose monitoring system comprising:

a medical testing input system, the medical testing input system coupled to the standard blood glucose meter via a gateway interface, the blood glucose meter receives the medical test blood sample and provides electronic data test output of the medical blood test sample to the medical testing input system, the medical testing system receives the electronic data test output and generates a test signal based on the electronic data test output from the medical test blood sample;

a computer-based audiovisual feedback system, the audiovisual feedback system includes a registry archive communicatively connected to the plurality of participants, a feedback application engine communicatively connected to the registry archive, an alteration engine communicatively connected to the feedback application engine and to the registry archive, and a system controller communicatively connected to the alteration engine, to the feedback application engine, and to the registry archive, the audiovisual feedback system receives the test signal from the medical testing input system, the feedback application engine includes a display application, the display application receives the test signal and generates a feedback audiovisual output signal based on the test signal;

an output device communicatively connected to the computer based audiovisual feedback system, the output device receives the feedback audiovisual output signal and provides an audio and visual output display based on the test output that corresponds to the blood glucose level of the donating participant at the time the blood sample was received by the blood glucose meter, the audio and visual output display is based on a continuity of predetermined musical tones and predetermined colors, respectively, each tone and color corresponding to a predetermined physiological emotional response diabetically experienced by the donating participant for each test signal to audiovisually indicate the blood glucose level received by the medical testing input system from the donating participant, the display audio visual output display includes an interface for a donating participant to make musical compositions and visual display compositions based on a series of test outputs provided by the donating participant to the audiovisual feedback system;

the system controller operates the output device to warn the donating participant to interactively control the rate of medication provided to the donating participant by prompting the donating participant to respond to the warning by providing another feedback audiovisual input signal to the output device; and the computer-based audiovisual feedback system generates a template header, the template header couples the audio visual displays to the donating participant's electronic medical records.

2. The blood glucose monitoring system according to claim 1 wherein the system controller stores the another feedback audiovisual output signal in memory to predict the response time of the donating participant and change the frequency of warnings from the output device based on the response time prediction, via the alteration engine.

3. The blood glucose monitoring system according to claim 1 wherein a feedback audiovisual input provides at least one musical note.

4. The blood glucose monitoring system according to claim 1 wherein a feedback audiovisual input signal is derived from the eye movement of the donating participant.

5. The blood glucose monitoring system according to claim 1 wherein the feedback application engine generates a continuous audio display and a continuous visual display by combining each consecutive feedback audiovisual signal received to form an electronic audiovisual playback file corresponding to the donating participant.

6. The blood glucose monitoring system according to claim 1 wherein the alteration engine, responsive to the feedback audiovisual input signal, generates a command signal to trigger the system controller to control the rate of medication provided to the donating participant responsive to the feedback audiovisual input signal of the another participant.

7. The blood glucose monitoring system according to claim 1 wherein the audiovisual feedback system controls the rate medication to the donating participant response to a feedback audiovisual input of another participant within a social network.

8. A health monitoring system, the health monitoring system communicatively connects with a meter for receiving a medical test sample from a donating participant from a plurality of participants, the health monitoring system comprising: a medical testing input system, the medical testing input system coupled to the meter via a gateway interface, the meter receives the medical test sample and provides electronic data test output of the medical test sample to the medical testing input system, the medical testing input system receives the electronic data test output and generates a test signal based on the electronic data test output from the medical test sample; a computer-based audiovisual feedback system, the audiovisual feedback system includes a registry archive communicatively connected to the plurality of participants, a feedback application engine communicatively connected to the registry archive, an alteration engine communicatively connected to the feedback application engine and to the registry archive, and a system controller communicatively connected to the alteration engine, to the feedback application engine, and to the registry archive, the audiovisual feedback system receives the test signal from the medical testing input system, the feedback application engine includes a display application, the display application receives the test signal and generates a feedback audiovisual output signal based on the test signal; an output device communicatively connected to the computer based audiovisual feedback system, the output device receives the feedback audiovisual output signal and provides an audio and visual output display based on the test output that corresponds to the metered level of the donating participant at the time the medical test sample was received by the meter, the audio and visual output display is based on a continuity of predetermined musical tones and predetermined colors, respectively, each tone and color corresponding to a predetermined physical emotion experienced by the donating participant for each test signal to audiovisually indicate the metered level received by the medical testing input system to the donating participant, the display audio visual output display includes an interface for a donating participant to make musical compositions and visual display compositions based on a series of test outputs provided by the donating participant to the audiovisual feedback system; the system controller operates the output device to warn the donating participant to interactively control the rate of medication provided to the donating participant by prompting the donating participant to respond to the warning by providing an other feedback audiovisual input signal to the output device; and the computer-based audiovisual feedback system generates a template header, the template header couples the audio visual displays to the donating participant's electronic medical records.

9. The health monitoring system according to claim 8 wherein the output device includes a personal area network device having an audio and visual output display coupled to furniture.

10. The health monitoring system according to claim 9 wherein the furniture includes a lamp for providing a visual display of the donating participant's metered status and whereby the visual display interacts with the donating participant by providing visual information to permit the donating participant to dynamically control the rate of medication provided to the donating participant.

11. The health monitoring system according to claim 9 wherein the furniture includes a speaker for providing an audio display of the donating participants metered status and whereby the audio display interacts with the donating participant by providing audio information to permit donating participant to dynamically control the rate of medication provided to the donating participant.

12. The health monitoring system according to claim 9 wherein the furniture includes a lamp for providing a visual display of the donating participant's metered status and whereby the visual display interacts with a system controller by providing signaled information to permit a medical injector to dynamically control the rate of medication provided to the donating participant.

13. The health monitoring system according to claim 9 wherein the furniture includes a speaker for providing an audio display of the donating participants metered status and whereby the audio display interacts with a system controller by providing signaled information to permit a medical injector to dynamically control the rate of medication provided to the donating participant.

* * * * *